(12) United States Patent
Smith et al.

(10) Patent No.: US 11,256,309 B2
(45) Date of Patent: Feb. 22, 2022

(54) METHODS AND DEVICES FOR MANIPULATING TEMPERATURE

(71) Applicant: EMBR Labs Inc., Somerville, MA (US)

(72) Inventors: Matthew J. Smith, Cambridge, MA (US); Kristen Warren, Cambridge, MA (US); David Cohen-Tanugi, Somerville, MA (US); Samuel Shames, Cambridge, MA (US)

(73) Assignee: EMBR Labs Inc., Boston, MA (US)

( * ) Notice: Subject to any disclaimer, the term of this patent is extended or adjusted under 35 U.S.C. 154(b) by 8 days.

(21) Appl. No.: 16/344,577

(22) PCT Filed: Nov. 9, 2017

(86) PCT No.: PCT/US2017/060822
§ 371 (c)(1),
(2) Date: Apr. 24, 2019

(87) PCT Pub. No.: WO2018/089609
PCT Pub. Date: May 17, 2018

(65) Prior Publication Data
US 2020/0050248 A1 Feb. 13, 2020

Related U.S. Application Data

(60) Provisional application No. 62/420,481, filed on Nov. 10, 2016.

(51) Int. Cl.
| | | |
|---|---|---|
| G05B 15/02 | (2006.01) | |
| G06F 1/20 | (2006.01) | |
| A61F 7/02 | (2006.01) | |

(52) U.S. Cl.
CPC ............. *G06F 1/206* (2013.01); *G05B 15/02* (2013.01); *A61F 7/02* (2013.01)

(58) Field of Classification Search
CPC ............ G05F 1/206; G05B 15/02; A61F 7/02
See application file for complete search history.

(56) References Cited

U.S. PATENT DOCUMENTS

| | | |
|---|---|---|
| 4,277,671 A | 7/1981 | Mori et al. |
| 4,585,002 A | 4/1986 | Kissin |
| (Continued) | | |

FOREIGN PATENT DOCUMENTS

| | | |
|---|---|---|
| JP | S62-82963 A | 4/1987 |
| JP | 2004-173750 A | 6/2004 |
| (Continued) | | |

OTHER PUBLICATIONS

International Search Report and Written Opinion for International Application No. PCT/US2017/060822, dated Jan. 17, 2018.

(Continued)

*Primary Examiner* — Gary Collins
(74) *Attorney, Agent, or Firm* — Wolf, Greenfield & Sacks, P.C.

(57) ABSTRACT

Methods and devices for manipulating the temperature of a surface are generally provided. The present disclosure relates to a device including one or more heating and/or cooling elements, or other suitable thermal adjustment apparatus(es), placed near a surface, such as the skin of a user. The device may be configured to generate one or more (optionally alternating) thermal profiles at the surface, which may include a series of thermal pulses and/or essentially continuous or semi-continuous thermal input, which may vary over time. Such thermal profiles, when suitably applied, may provide enhanced thermal sensations for a user which, in some cases, may provide the user with a more pleasurable thermal experience than would otherwise be the case without the generation of the thermal profiles. In some embodiments, an alternating thermal profile may include an (Continued)

average frequency, an oscillation window, and/or an average temperature, each of which may be adjustable.

21 Claims, 18 Drawing Sheets

(56) References Cited

U.S. PATENT DOCUMENTS

| | | | |
|---|---|---|---|
| 4,860,748 A | 8/1989 | Chiurco et al. | |
| 5,746,702 A | 5/1998 | Gelfgat et al. | |
| 7,713,295 B2 | 5/2010 | Ahn et al. | |
| 7,871,427 B2 | 1/2011 | Dunbar et al. | |
| 8,083,786 B2 | 12/2011 | Gafni et al. | |
| 8,267,983 B2 | 9/2012 | Rogers et al. | |
| 8,397,518 B1 | 3/2013 | Vistakula | |
| 9,849,024 B2 | 12/2017 | Mandel | |
| 2006/0195168 A1* | 8/2006 | Dunbar | A61F 7/007 607/108 |
| 2010/0057168 A1* | 3/2010 | Slade | A61F 7/007 607/99 |
| 2014/0194958 A1* | 7/2014 | Chabal | A61F 7/02 607/96 |
| 2015/0101788 A1* | 4/2015 | Smith | A61F 7/007 165/201 |
| 2016/0030234 A1* | 2/2016 | Lofy | A61M 13/003 607/107 |
| 2016/0262924 A1 | 9/2016 | Abreu | |
| 2017/0056238 A1 | 3/2017 | Yi et al. | |
| 2021/0089097 A1 | 3/2021 | Smith et al. | |

FOREIGN PATENT DOCUMENTS

| | | |
|---|---|---|
| WO | 2016/149117 A1 | 8/2016 |
| WO | WO 2019/043482 A1 | 3/2019 |
| WO | WO 2019/046605 A1 | 3/2019 |

OTHER PUBLICATIONS

[No Author Listed] Poster for Wristify: Thermal comfort, reimagined. MIT Department of Materials Science and Engineering, Mad Mec. Oct. 15, 2013, 1 page.

* cited by examiner

METHODS AND DEVICES FOR MANIPULATING TEMPERATURE

RELATED APPLICATIONS

This application is a National Stage filing under 35 U.S.C. § 371 of international application serial number PCT/US2017/060822, filed on Nov. 9, 2017, which claims the benefit of priority under 35 U.S.C. § 119(e) of U.S. provisional application Ser. No. 62/420,481, filed Nov. 10, 2016, the disclosures of each of which are incorporated herein in their entirety.

FIELD

The present disclosure relates generally to methods and devices for manipulating temperature of a surface.

BACKGROUND

Substantial amounts of energy are used each year by heating, ventilation and air conditioning (HVAC) systems, for keeping spaces within homes, offices, buildings, and other enclosures within comfortable temperature ranges. Despite the significant amounts of energy expended, thermal discomfort still remains a major cause of dissatisfaction within building environments, largely due to wide variance in personal preference. In many cases, an indoor space considered to be optimally conditioned might only be satisfying to 80% of the occupants at a given time. Conventional HVAC systems are incapable of providing the spatial and temporal variation in temperature that would be necessary for each occupant to feel comfortable, focused, and productive in his/her respective environment.

Existing wearable devices for thermal regulation (e.g., clothing) are generally passive in that they do not generate or absorb heat but merely serve to insulate the wearer from the outside temperature. Despite rapid improvements in the field of active wearable devices, including watches, accelerometers, motion sensors, etc., there is a gap in the understanding of wearable devices that actively work to enhance the thermal comfort of the wearer.

SUMMARY

Methods and devices for manipulating the temperature of a surface are provided.

In one aspect, devices for manipulating a temperature of a surface are provided. In some embodiments, the device comprises at least one heating and/or cooling element constructed and arranged to be disposed adjacent the surface and a controller in electrical communication with the at least one heating and/or cooling element, the controller configured to cause the at least one heating and/or cooling element to generate a thermal profile at a region of the at least one heating and/or cooling element adjacent the surface, the thermal profile comprising a first portion comprising a ramp profile, a second portion comprising a first alternating temperature profile, and at least a third portion comprising at least a second alternating temperature profile, different than the first alternating temperature profile.

In some embodiments, the device comprises at least one heating and/or cooling element constructed and arranged to be disposed adjacent the surface and a controller in electrical communication with the at least one heating and/or cooling element, the controller configured to cause the at least one heating and/or cooling element to generate a thermal profile at a region of the at least one heating and/or cooling element adjacent the surface, the alternating thermal profile comprising an average temperature, an average frequency, and an oscillation window, wherein the controller is configured to modify at least one of the average temperature, the average frequency, and the oscillation window.

In another aspect, methods for manipulating a temperature of a surface are provided. In some embodiments, the method comprises positioning a region of at least one heating and/or cooling element adjacent to the surface, and generating a thermal profile at the region of the at least one heating and/or cooling element adjacent the surface, wherein generating the thermal profile includes generating a first thermal profile portion comprising a ramp profile, generating a second thermal profile portion comprising a first alternating temperature profile, and generating a third thermal profile portion comprising a second alternating temperature profile different than the first alternating temperature profile.

In some embodiments, the method comprises positioning a region of at least one heating and/or cooling element adjacent to the surface, generating an alternating thermal profile at the region of the at least one heating and/or cooling element adjacent the surface, wherein the alternating thermal profile comprises an average frequency, an average temperature, and an oscillation window, and modifying at least one of the average frequency, the average temperature, and the oscillation window.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figure, which is schematic and is not intended to be drawn to scale. In the figure, each identical or nearly identical component illustrated is typically represented by a single numeral. For purposes of clarity, not every component is labeled, nor is every component of each embodiment of the invention shown where illustration is not necessary to allow those of ordinary skill in the art to understand the invention. In the figures.

DETAILED DESCRIPTION

Figure 1A:
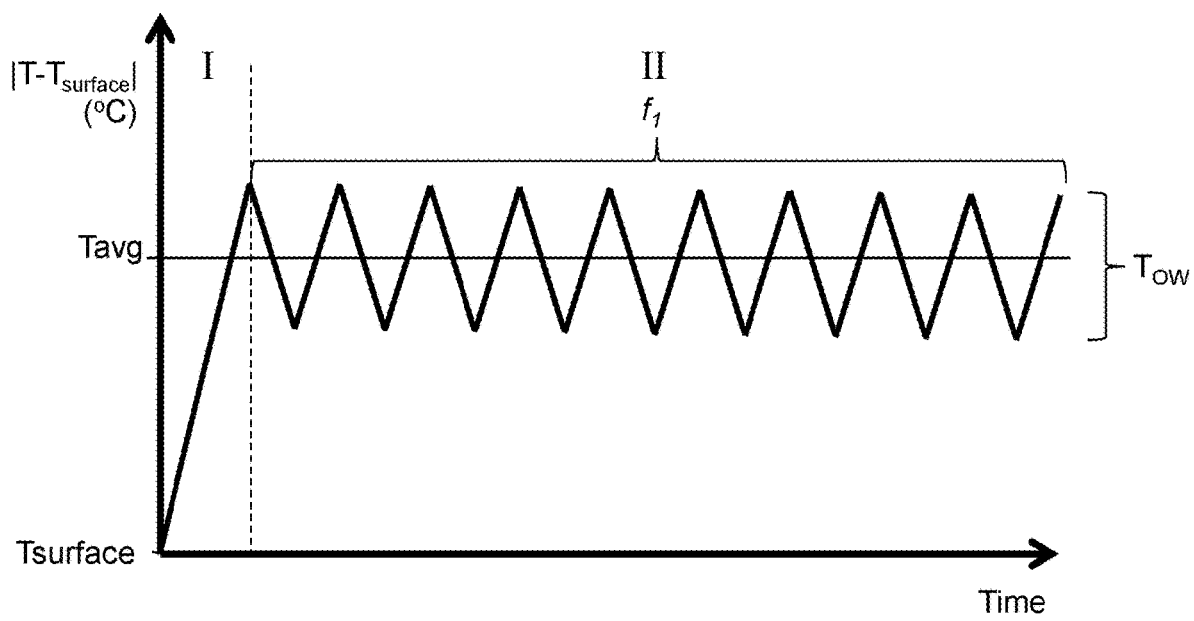
FIG. 1A is a schematic representation of a thermal profile generated by a device according to one set of embodiments.

Methods and devices for manipulating the temperature of a surface are generally provided. The present disclosure relates to a device that includes one or more heating and/or cooling elements, or other suitable thermal adjustment apparatus(es) (e.g., at least a thermoelectric material), placed near a surface, such as the skin of a user. The device may be configured to generate one or more (optionally alternating) thermal profiles at the surface, which may be accomplished by generating a series of thermal pulses and/or essentially continuous or semi-continuous thermal input, which may vary over time. Such thermal profiles, when suitably applied, may result in an enhanced thermal sensation for a user which, in some cases, may provide the user with a more pleasurable thermal experience than would otherwise be the case without the generation of the thermal profiles. Advantageously, in some embodiments, one or more properties of each thermal profile may be adjusted in order to provide continuous or semi-continuous enhanced thermal sensation to the user. As further described herein, an alternating thermal profile may include an average frequency, an oscillation window, and/or an average temperature, each of which may be adjustable. In some embodiments, the thermal profile (or one or more properties of the alternating thermal profile) may be adjusted in response to a signal sent to the device generated by a sensor and/or a user input.

Under conventional usage, heating and/or cooling elements, or other temperature adjustment devices (e.g., thermoelectric materials, resistive heaters), for heating or cooling are generally operated in steady-state, i.e., under constant applied temperature and/or electrical signal modes, so as to maintain long-time scale applications of heating or cooling. For example, such conventional methods are typically used for hot or cold pack compression therapy where it is desirable for the temperature to remain the same for long periods of time. In contrast, aspects of the present disclosure involve generating thermal profiles that are substantially adjustable, may be alternating, and which may result in continuous thermal stimulation for the human skin.

The term thermoelectric material is given its ordinary meaning in the art and refers to materials in which a temperature change is generated at a surface of the material upon application of an electric potential (e.g., voltage and corresponding current), in accordance with the thermoelectric effect (e.g., often referred to by other names such as the Peltier, Thomson, and Seebeck effects). Any suitable thermoelectric may be employed, a number of which are described further below. It should be understood that, while a portion of the description herein describes thermoelectric materials, the present disclosure is not limited to thermoelectric materials, and other thermal adjustment apparatuses may be employed where appropriate.

The term resistive heater is given its ordinary meaning in the art and refers to materials in which a temperature increase is generated at a surface of the material upon application of an electric potential (e.g., voltage and corresponding current), in accordance with joule heating. Any suitable resistive heating element may be employed, which could use any electrical conductor with sufficient resistance to generate joule heating. It should be understood that, while a portion of the description herein describes resistive heating elements, the present disclosure is not limited to resistive heating, and other heating apparatuses may be employed where appropriate.

The inventors have recognized, unexpectedly, that varying the thermal profile applied to the surface of human skin in a certain manner, for example, by generating alternating thermal profiles and adjusting one or more properties of the alternating thermal profiles may give rise to an enhanced perception of a particular heating or cooling effect for the individual. For example, the alternating thermal profile may be used and/or adjusted to overcome sensory adaptation. Without wishing to be bound by theory, such alternating thermal profiles may leverage the behavior of thermoreceptors in human skin to create periodic sensations of consistent intensity that overcome thermal adaptation. In some embodiments, the alternating thermal profile may be adjusted to tailor the profile to the needs of a user (e.g., to enhance thermal comfort). That is, when subject to thermal profiles in accordance with embodiments of the present disclosure, the perceived strength of this heating/cooling effect is comparable to actual changes in temperature that are much larger in magnitude than may be applied to the individual.

By generating alternating thermal profiles at the surface of human skin according to certain embodiments, properties (e.g., average frequency, average temperature, oscillation window) which may or may not be adjusted, thermoreceptors of the skin may be controllably stimulated. The inventors have appreciated that, in responding to heating and/or cooling at the surface of the skin, thermoreceptors may have a tendency to adapt (sensory adaptation) and, once accustomed to the immediate environment, become desensitized to the initial stimulus. This is analogous to the desensitization of skin to the touch of an external stimuli, such as clothing or some other stimulus to which the senses may become accustomed.

The inventors have discovered, in particular, that by generating a thermal profile, for example an alternating thermal profile, at the surface of human skin having particular combinations of parameters, such as average frequency, average temperature, oscillation window, etc., as described in more detail herein, the effects of adaptive desensitization can be mitigated or otherwise reduced, and the perceived effects of cooling and/or heating can be enhanced. As compared to the desensitization that may occur in a cooled or heated room, the devices described herein may be able to continuously provide a user with an enhanced thermal experience, e.g., a pleasant feeling of cooling and/or heating, according to his/her preferences. As noted above, due to the manner in which the thermal profile is generated and/or adjusted, when the device is in operation, may promote, for example, parasympathetic engagement in the autonomic nervous system of the human body.

In some embodiments, the device includes one or more heating and/or cooling elements (e.g., thermoelectric materials) that may be positioned directly adjacent to the skin of a user. An electrical input, for example in the form of an electrical signal, may be applied to the heating and/or cooling element(s) so as to manipulate the temperature of the surface of the skin, for example, in the form of thermal profile, such as an alternating thermal profile. Though, it can be appreciated that any suitable heating and/or cooling element may be employed; for example, a resistive heating device, convective thermal device, radiative thermal device, or any other suitable apparatus that may be able to generate a series of warming and/or cooling thermal pulses may be used. In certain embodiments, thermoelectric materials are preferred.

In certain embodiments, the application of an adjustable, alternating thermal profile to the surface of human skin may interact with one or more physiological systems such that a physiological response is generated. For example, an adjustable alternating thermal profile may be used to modify one or more of vasoconstriction/vasodilation, respiration rate, heart rate, skin temperature, sweating, shivering, sympathetic response(s) (e.g., by the autonomic nervous system), perceived temperature on the skin, and/or thermal pleasure in a human subject (e.g., the user).

In some embodiments, the device comprises at least one heating and/or cooling element constructed and arranged to be disposed adjacent a surface (e.g., a surface of skin) and a controller in electrical communication with the at least one heating and/or cooling element. In certain embodiments, the controller is configured to cause at least one heating and/or cooling element to generate an alternating thermal profile at a region of the heating and/or cooling element adjacent (e.g., directly adjacent) the surface.

As used herein, when an element/component/layer/surface is referred to as being "adjacent" an element/component/layer/surface, it can be directly adjacent to the element/component/layer/surface, or an intervening element/component/layer/surface also may be present. A layer that is "directly adjacent" another element/component/layer/surface means that no intervening element/component/layer/surface is present.

In some embodiments, the thermal profile comprises one or more portions including a ramp profile portion and/or one or more alternating thermal profile portions. For example, as illustrated schematically in FIG. 1A, the thermal profile may comprise a first portion comprising a ramp profile portion (regime I) where a temperature of the device and surface is driven to a first temperature that may be greater than or less than the initial surface temperature $T_{surface}$. This may correspond to either cooling or heating of the surface. The temperature is then cyclically varied between the first temperature and a second temperature in a second portion comprising an alternating thermal profile portion (regime II). Each cycle includes a first portion of the cycle that drives the surface temperature from the first temperature to the second temperature and a second portion of the cycle that drives the surface temperature from the second temperature to the first temperature. Those of ordinary skill in the art would understand that while FIGS. 1A-1D show schematically a saw-tooth thermal profile for cycling the device and surface temperature between the first and second temperature, that these profiles are for illustrative purposes and that the actual thermal profile may have substantially linear, non-linear, exponential (e.g., exponential growth, exponential decay), polynomial (quadratic, cubed, etc.), irregular (e.g., following a piecewise function), sinusoidal, or other suitable behaviors. In some embodiments, the alternating thermal profile portion may have an average frequency, $f_1$, an average temperature, $T_{avg}$, and an oscillation window, $T_{ow}$. The oscillation window is the difference between the maximum and minimum temperature for a given alternating thermal profile. In certain embodiments the oscillation window may be twice the average amplitude of the alternating thermal profile portion. The average temperature, $T_{avg}$, may be the average temperature around which the alternating thermal profile portion alternates. In some embodiments, the average temperature, may also be the inflection point between the average minimum and average maximum temperatures. In some embodiments, the temperature of the surface created by the alternating thermal profile portion at any given time may be measured with respect to the initial temperature of the surface, $T_{surface}$ (measured immediately before generating the thermal profile).

For the sake of clarity the above embodiments of FIGS. 1A-1D, and the embodiments described in FIG. 1E below, the temperature has been depicted using a magnitude of a difference between the instantaneous temperature applied by the device to a surface, and an initial temperature of the surface a device is disposed against prior to operation. Accordingly, the depicted and described temperature profiles may refer to either cooling and/or heating processes where the temperature applied by a device to a surface changes from the surface temperature to a temperature between or equal to a first temperature and a second temperature. The temperature of the device, and the associated surface, may then be cyclically oscillated between these first and second temperatures. Thus, such an operation may be thought to cyclically oscillate a temperature of the device and surface between a first temperature with a first larger magnitude difference relative to an initial surface temperature and a second temperature with a second temperature with a smaller magnitude difference relative to the initial surface temperature.

In some embodiments, the absolute difference between the average temperature, $T_{avg}$, during the alternating temperature profile and the initial temperature of the surface (e.g., the temperature of the skin) is greater than 0° C., greater than or equal to 2° C., greater than or equal to 4° C., greater than or equal to 6° C., greater than or equal to 8° C., greater than or equal to 10° C., greater than or equal to 12° C., greater than or equal to 14° C., greater than or equal to 16° C., or greater than or equal to 18° C. In certain embodiments, the absolute difference between the average temperature, $T_{avg}$, and the temperature of the surface, is less than or equal to 20° C., less than or equal to 18° C., less than or equal to 16° C., less than or equal to 14° C., less than or equal to 12° C., less than or equal to 10° C., less than or equal to 8° C., less than or equal to 6° C., less than or equal to 4° C., or less than or equal to 2° C. Combinations of the above-referenced ranges are also possible (e.g., greater than 0° C. and less than or equal to 20° C.). Other ranges are also possible.

In certain embodiments, the average oscillation window is greater than 0° C., greater than or equal to 2° C., greater than or equal to 4° C., greater than or equal to 6° C., greater than or equal to 8° C., greater than or equal to 10° C., greater than or equal to 12° C., greater than or equal to 14° C., greater than or equal to 16° C., or greater than or equal to 18° C. In certain embodiments, the average oscillation window is less than or equal to 20° C., less than or equal to 18° C., less than or equal to 16° C., less than or equal to 14° C., less than or equal to 12° C., less than or equal to 10° C., less than or equal to 8° C., less than or equal to 6° C., less than or equal to 4° C., or less than or equal to 2° C. Combinations of the above-referenced ranges are also possible (e.g., greater than 0° C. and less than or equal to 20° C.). Other ranges are also possible.

In some embodiments, the average frequency of the alternating thermal profile portion may be greater than or equal to 0.0025 Hz, greater than or equal to 0.005 Hz, greater than or equal to 0.01 Hz, greater than or equal to 0.05 Hz, greater than or equal to 0.1 Hz, greater than or equal to 0.5 Hz, greater than or equal to 1 Hz, greater than or equal to 2 Hz, greater than or equal to 5 Hz, greater than or equal to 10 Hz, or greater than or equal to 20 Hz. In certain embodiments, the average frequency of the alternating thermal profile may be less than or equal to 50 Hz, less than or equal to 20 Hz, less than or equal to 10 Hz, less than or equal to 5 Hz, less than or equal to 2 Hz, less than or equal to 1 Hz, less than or equal to 0.5 Hz, less than or equal to 0.1 Hz, less than or equal to 0.05 Hz, less than or equal to 0.01 Hz, less than or equal to or less than or equal to 0.005 Hz. Combinations of the above-referenced ranges are also possible (e.g., between or equal to 0.0025 Hz and 50 Hz as well as between or equal to 0.01 Hz and 1.0 Hz). Other ranges are also possible.

In some embodiments, the alternating thermal profile portion may have a particular average rate of temperature change. The average rate of temperature change is the average of the oscillation window over an interval of time multiplied by the average frequency of the alternating thermal profile over the same interval of time. In some embodiments, the average rate of temperature change of the alternating thermal profile portion is greater than or equal to greater than or equal to 0.1° C./sec, greater than or equal to 0.2° C./sec, greater than or equal to 0.3° C./sec, greater than or equal to 0.5° C./sec, greater than or equal to 0.7° C./sec, greater than or equal to 1.0° C./sec, greater than or equal to 1.5° C./sec, greater than or equal to 2.0° C./sec, greater than or equal to 3.0° C./sec, greater than or equal to 5.0° C./sec, or greater than or equal to 7.0° C./sec. In certain embodiments, the average rate of temperature change of the alternating thermal profile is less than 10.0° C./sec, less than 7.0° C./sec, less than 5.0° C./sec, less than 3.0° C./sec, less than 2.0° C./sec, less than 1.5° C./sec, less than 1.0° C./sec, less than 0.7° C./sec, less than 0.5° C./sec, less than 0.3° C./sec, or less than 0.2° C./sec. Combinations of the above-referenced ranges are possible (e.g., between 0.1° C./sec and 10.0° C./sec, between 0.1° C./sec and 5.0° C./sec, between 0.3° C./sec and 3.0° C./sec, between 0.3° C./sec and 1.0° C./sec, between 0.3° C./sec and 0.8° C./sec, between 0.5° C./sec and 3.0° C./sec). Other ranges are also possible.

Advantageously, an average frequency, an average oscillation window, an average temperature, and/or an average rate of temperature change in the one or more ranges described above may mitigate and/or reduce the effects of adaptive desensitization to temperature and/or create other desired sensory perceptions or experiences.

In some embodiments, one or more of the average frequency, the average oscillation window, the average temperature, and/or the average rate of temperature change may be adjusted. For example, in some embodiments, the controller is configured to cause the at least one heating and/or cooling element to generate a thermal profile at a region of the at least one heating and/or cooling element adjacent the surface. In certain embodiments, the controller is configured to modify at least one of the average temperature, the average frequency, and the oscillation window.

Figure 1B:
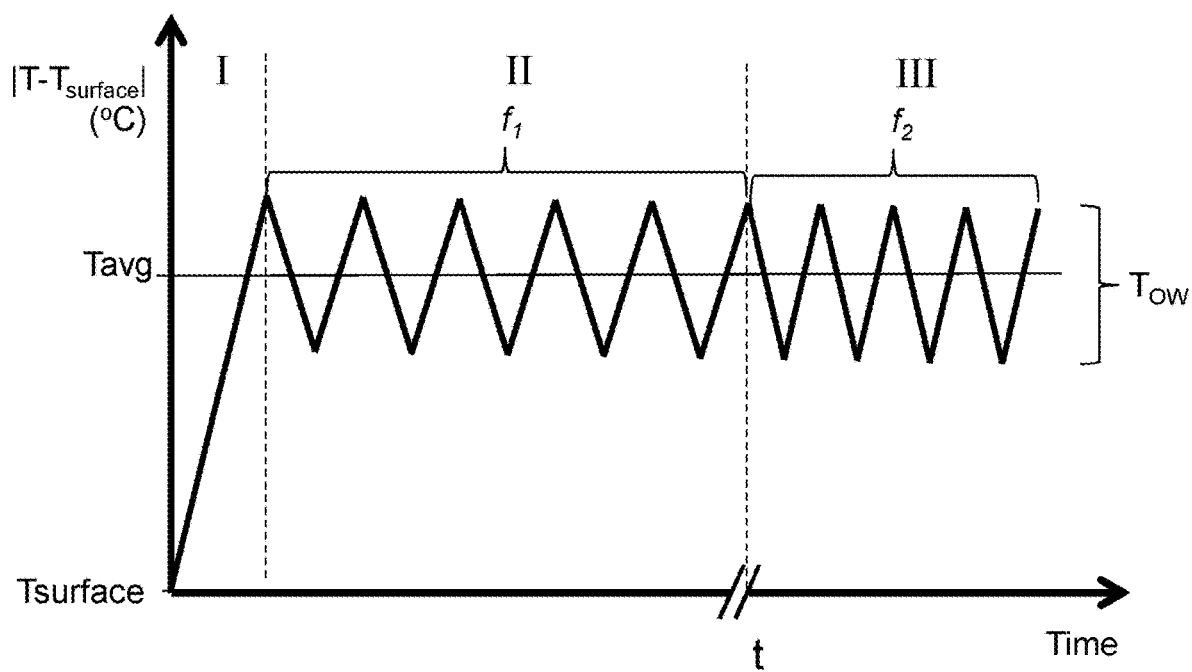
FIG. 1B is a schematic representation of a thermal profile generated by a device according to one set of embodiments.
Figure 1C:
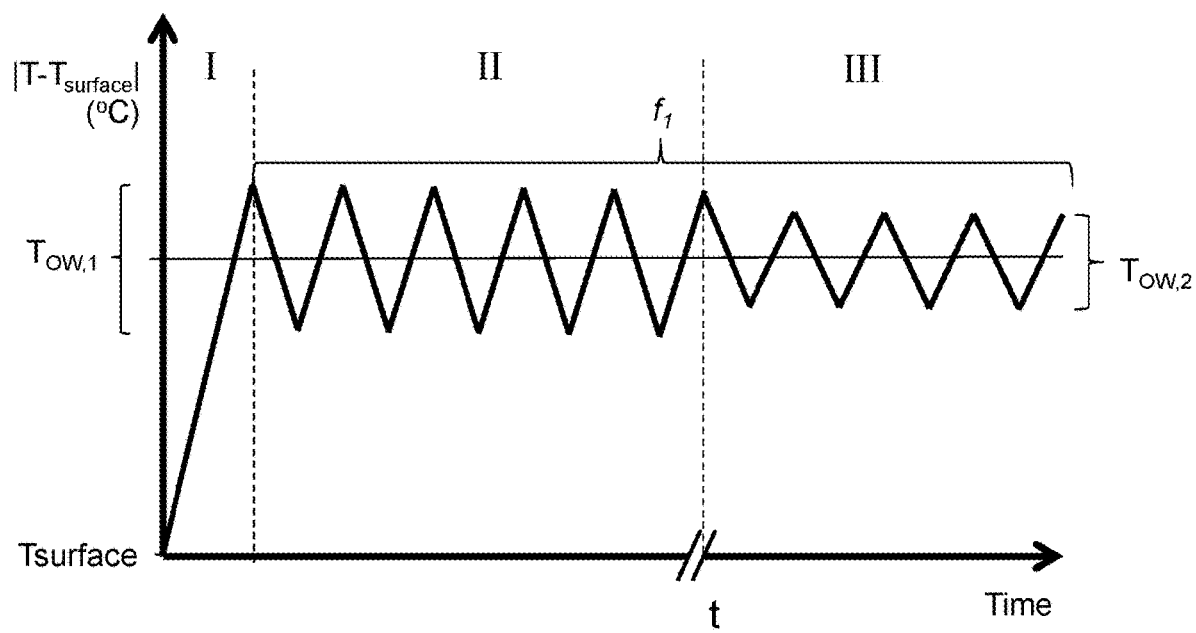
FIG. 1C is a schematic representation of a thermal profile generated by a device according to one set of embodiments.
Figure 1D:
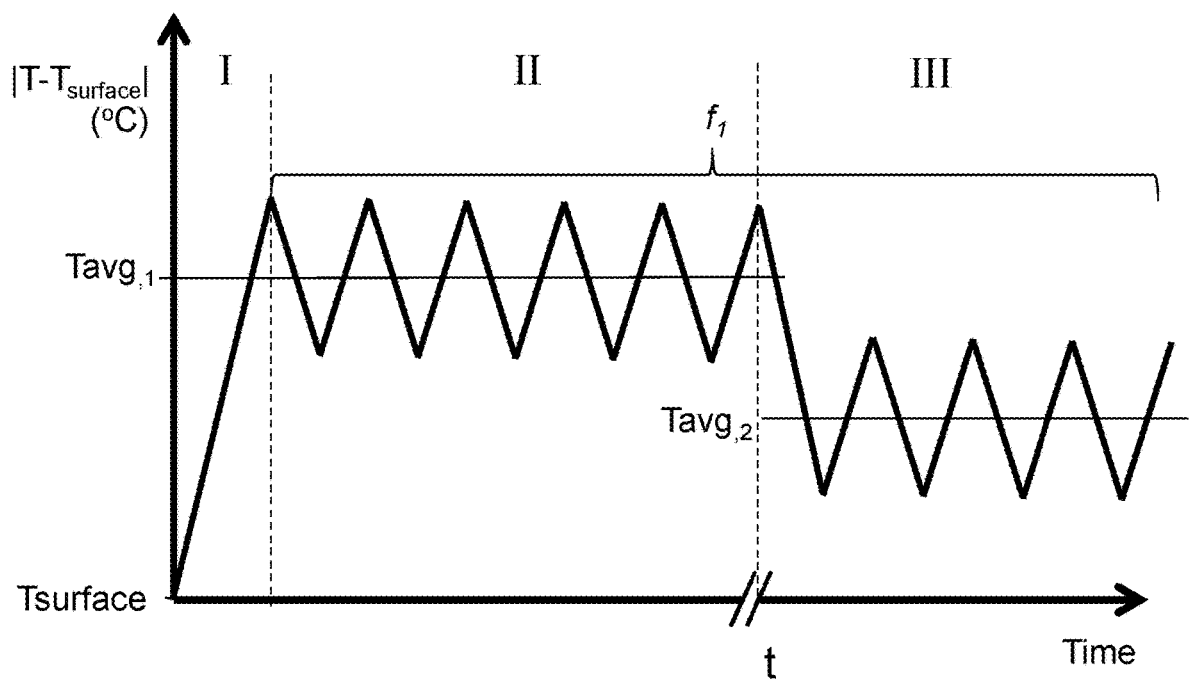
FIG. 1D is a schematic representation of a thermal profile generated by a device according to one set of embodiments.
Figure 1E:
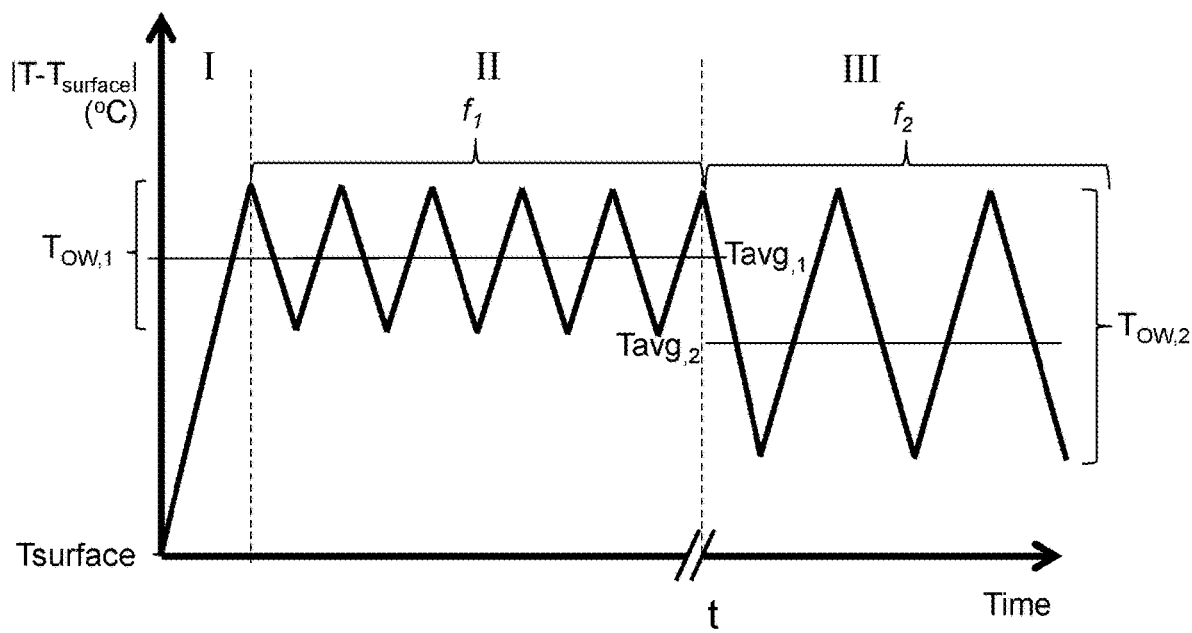
FIG. 1E is a schematic representation of a thermal profile generated by a device according to one set of embodiments.

As shown illustratively in FIGS. 1B-1D, in some embodiments, the thermal profile may comprise a first portion comprising a ramp profile portion (regime I), a second portion comprising a first alternating thermal profile portion (regime II), and at least a third portion comprising at least a second alternating thermal profile portion (regime III). In some embodiments, at least one property of the second alternating thermal profile portion is different than the first alternating thermal profile portion. For example, in some embodiments, the first alternating thermal profile portion has a first average temperature, a first average frequency, and a first oscillation window, while the second alternating thermal profile portion has a second average temperature, a second average frequency, and a second oscillation window. One or more of the first average temperature, the first average frequency, and the first oscillation window may be different than the second average temperature, the second average frequency, and the second oscillation window, respectively.

In some embodiments, the first average frequency and the second average frequency are the same. In some embodiments, the first average frequency and the second average frequency are different. For example, as shown illustratively in FIG. 1B, in some embodiments, the thermal profile comprises a first portion comprising a ramp profile portion (regime I), a second portion comprising a first alternating thermal profile portion (regime II), and a third portion comprising a second alternating thermal profile portion having an average frequency, $f_2$, different than an average frequency, $f_1$, of the first alternating thermal profile portion.

In some embodiments, the first average oscillation window and the second average oscillation window are the same. In some embodiments, the first average oscillation window and the second average oscillation window are different. For example, as shown illustratively in FIG. 1C, in some embodiments, the thermal profile comprises a first portion comprising a ramp profile portion (regime I), a second portion comprising a first alternating thermal profile portion (regime II), and a third portion comprising a second alternating thermal profile portion having an average oscillation window, $T_{ow,2}$, different than an average oscillation window, $T_{ow,1}$, of the first alternating thermal profile portion.

In some embodiments, the first average temperature and the second average temperature are the same. In some embodiments, the first average temperature and the second average temperature are different. For example, as shown illustratively in FIG. 1D, in some embodiments, the thermal profile comprises a first portion comprising a ramp profile portion (regime I), a second portion comprising a first alternating thermal profile portion (regime II), and a third portion comprising a second alternating thermal profile portion having an average temperature window, $T_{avg,2}$, different than an average oscillation window, $T_{avg,1}$, of the first alternating thermal profile portion.

In some embodiments, the ratio of the second average frequency to the first average frequency is greater than or equal to 0.0025:1, greater than or equal to 0.005:1, greater than or equal to 0.01:1, greater than or equal to 0.05:1, greater than or equal to 0.1:1, greater than or equal to 0.5:1, greater than or equal to 2:1, greater than or equal to 5:1, greater than or equal to 10:1, greater than or equal to 25:1, greater than or equal to 50:1, greater than or equal to 100:1, or greater than or equal to 250:1. In certain embodiments, the ratio of the second average frequency to the first average frequency is less than or equal to 500:1, less than or equal to 250:1, less than or equal to 100:1, less than or equal to 50:1, less than or equal to 25:1, less than or equal to 10:1, less than or equal to 5:1, less than or equal to 2:1, less than or equal to 0.5:1, less than or equal to 0.1:1, less than or equal to 0.05:1, less than or equal to 0.01:1, or less than or equal to 0.005:1. Combinations of the above-referenced ranges are possible (e.g., greater than or equal to 0.0025:1 and less than or equal to 500:1). Other ranges are also possible.

In certain embodiments, the ratio of the second average temperature to the first average temperature is greater than or equal to 0.01:1, greater than or equal to 0.05:1, greater than or equal to 0.1:1, greater than or equal to 0.5:1, greater than or equal to 2:1, greater than or equal to 5:1, or greater than or equal to 10:1. In some embodiments, the ratio of the second average temperature to the first average temperature is less than or equal to 20:1, less than or equal to 10:1, less than or equal to 5:1, less than or equal to 2:1, less than or equal to 0.5:1, less than or equal to 0.1:1, or less than or equal to 0.05:1. Combinations of the above referenced ranges are possible (e.g., greater than or equal to 0.01:1 and less than or equal to 20:1). Other ranges are also possible. Ratios of temperatures described herein refer to temperature as measured in degrees Celsius.

In some embodiments, the percent difference between the second average oscillation window and the first average oscillation window is greater than or equal to 0.01:1, greater than or equal to 0.05:1, greater than or equal to 0.1:1, greater than or equal to 0.5:1, greater than or equal to 2:1, greater than or equal to 5:1, or greater than or equal to 10:1. In some embodiments, the ratio of the second average temperature to the first average temperature is less than or equal to 20:1, less than or equal to 10:1, less than or equal to 5:1, less than or equal to 2:1, less than or equal to 0.5:1, less than or equal to 0.1:1, or less than or equal to 0.05:1. Combinations of the above referenced ranges are possible (e.g., greater than or equal to 0.01:1 and less than or equal to 20:1). Other ranges are also possible. Ratios of oscillations windows described herein refer to temperature as measured in degrees Celsius. Those of ordinary skill in the art, based upon the teachings of this specification, would understand that the controller may be configured to change one or more (e.g., two or more) of the average temperature, average oscillation window, and average frequency independently, in relation to each other, at varying time internals, and/or simultaneously. In an exemplary embodiment, as shown illustratively in FIG. 1E, the thermal profile comprises a first portion comprising a ramp profile portion (regime I), a second portion comprising a first alternating thermal profile portion (regime II), and a third portion comprising a second alternating thermal profile portion having an average temperature window, $T_{avg,2}$, an average oscillation window, $T_{ow,2}$, and an average frequency, $f_2$, different than the average temperature window, $T_{avg,1}$, average oscillation window, $T_{avg}$, and average frequency, $f_2$, of the first alternating thermal profile portion. In some embodiments, the controller is configured adjust the alternating thermal profile portion (e.g., change one or more of the average frequency, average oscillation window, and average temperature) in response to an input from a user and/or a sensor.

As noted above, thermal profiles generated at the surface of the skin, in accordance with various embodiments, may provide a person with an enhanced thermal experience, resulting in a perceived heating or cooling sensation for the person, that is does not result in (or results in a diminished perception of) adaptive desensitization to temperature. For example, when the ambient temperature is cooler than is otherwise desirable, a user may set the device to a suitable heating mode where a thermal profile comprising a ramp profile and one or more alternating thermal profile portions may be generated at the surface of the user's skin cause the user to feel warmer within that environment. Conversely, in an uncomfortably warm ambient environment, the user may set the device to a suitable cooling mode, generating a thermal profile at the surface of the skin so as to cause the user to feel cooler. For each of the heating and cooling modes, in certain embodiments, the controller may be configured to allow a user to adjust various parameters (e.g., magnitude of average temperature change, magnitude of average frequency change, magnitude of average oscillation window change, etc.) based on preference.

Figure 2:
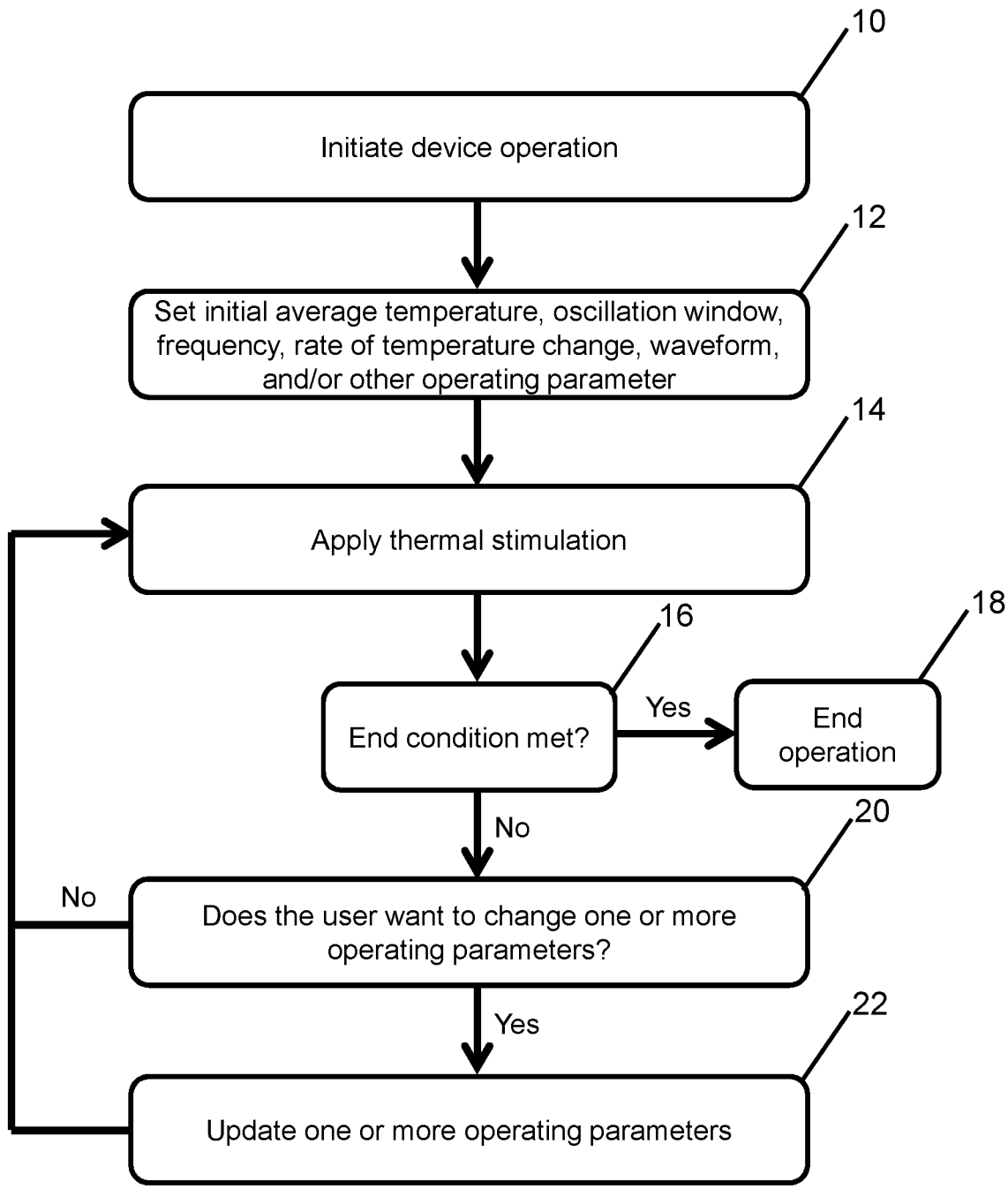
FIG. 2 is a schematic flow diagram of one embodiment of an operating method of a thermal device capable of applying thermal stimulation to a user.

FIG. 2 depicts one embodiment of a method for operating a device used to apply a desired type of thermal stimulation to a surface, such as a user's skin. In the depicted embodiment, the device operation is initiated at 10 using any appropriate input. For example, a user may press a button on the device or a button of a graphical user interface on a touch screen integrated on the device and/or located on a separate computing device such as a smart phone or tablet. A user may then set one or more initial operating parameters of the device including, but not limited to, a setpoint temperature (e.g. an average temperature, maximum temperature, minimum temperature, or similar operating temperature of the device), oscillation window, frequency, waveform, and/or any other appropriate operating parameters at 12. Specific ways of setting these parameters are elaborated on below. Further, while setting the parameters has been depicted as being separate and after initiating operation of the device, embodiments in which the initial operating parameters are set prior to initiation, correspond to the operating parameters used during the last operation cycle, and/or are set during initiation of the device are also contemplated as the disclosure is not so limited. In either case, after initiating operation of the device, the device may be operated to apply a desired thermal profile to a surface, such as a user's skin, at 14 where the temperature of the adjacent surface and a corresponding surface of the device are driven to provide a desired cooling and/or heating sensation to a user using thermal profiles similar to those described above in regards to FIGS. 1A-1E.

While a device applies a thermal stimulation to a user, a controller of the device may determine whether or not one or more end conditions for the thermal profile have been met at 16. Appropriate end conditions may include, but are not limited to, user termination, exceeding a duration threshold, meeting a maximum and/or minimum threshold operating temperature of one or more components of the device, and/or any other appropriate end condition. If the one or more end conditions are met the device may end operation at 18. Otherwise, a controller of the device may determine whether a user wants to change one or more of the operating parameters of the device at 20. If it is determined that a user wants to change one or more operating parameters, the one or more operating parameters may be updated at 22 as discussed further below prior to continuing to apply the desired thermal profile with the updated one or more operating parameters. Otherwise, the device may continue to apply the desired thermal profile until the one or more end conditions are met to terminate operation of the device.

In some embodiments, adjustments to the various operating parameters may be done prior to, during, and/or after operation of a device using any appropriate type of input including for example buttons, keypads, a graphical user interface using a touch screen, or any other appropriate type of input as previously described. For example, a device may include plus and minus buttons in addition to a set or enter button, though different types and/or arrangements of buttons are also contemplated. In one embodiment, a user may be prompted to enter, change, and/or confirm operating parameters, though embodiments in which no prompts are given and a user may simply change the operating parameters at will are also contemplated. The types of operating parameters that may be adjusted include, but are not limited to, a setpoint temperature (e.g. an average, minimum, and/or maximum temperature of a thermal profile), oscillation window, frequency, rate of temperature change, particular waveform shapes, and/or any other appropriate operating parameter.

Due to the large variability in thermal perception both among different individuals, and the same individual under different circumstances, it may be desirable to let a user determine a magnitude of a thermal sensation applied to the user during the ramp portion of a thermal profile. Specifically, in one embodiment, an first user input to a controller of the device may initiate operation of a device, i.e. may initiate the ramp profile or portion of a thermal profile to provide a desired cooling and/or warming sensation to a user. The user may then provide a second user input to indicate when a desired amount of thermal sensation has been provided to a user. For example, a user may provide the second user input to the controller when the device applies a desired temperature to the skin of the user. Thus, the second input may be used by the controller to set a setpoint temperature of the device including, for example, one or more of an average temperature, maximum temperature, and/or minimum temperature for a thermal profile applied by the device. The first and second user inputs to the controller of the device may correspond to any appropriate type of input. For example, the first and second inputs may correspond to two separate inputs such as two separate pushes of a keyboard, one or more buttons, an input button on a graphical user interface, gestures or taps from a user monitored with an IMU integrated with the device, or any other appropriate form of input as previously described. Alternatively, in some embodiments, the first and second user inputs may correspond to the pressing and release of a button. For example, a user may depress a button to provide the first user input to a controller to initiate operation of the device. The user may then release the button to provide the second user input to the controller to select the desired set point temperature such as an average, maximum, and/or minimum temperature to be used for a thermal profile applied to the user. In instances where a user does not provide the second input to the device controller until a maximum setpoint temperature of the thermal profile is reached, the controller may set the setpoint temperature as the maximum setpoint temperature for the thermal profile.

It should be understood that the above described types of user inputs to adjust the one or more operating temperatures of a device may be used both during an initial ramp portion of the device and during adjustments of the operating temperatures of the device during the cyclic portion of operation of the device. For example, in some embodiments, when it is desired to change one or more operating temperatures of a device during cyclic operation, a user input to a controller of the device may first indicate whether or not a temperature magnitude (i.e. a temperature difference relative to an initial surface temperature), an oscillating window, frequency, rate of change, or other parameter should be increased or decreased. The user may then provide subsequent user inputs to initiate the change and set the desired operating parameter as described above. For example, a user may press and hold a temperature increase or decrease button and/or the user may provide a separate input to indicate whether to increase or decrease a magnitude of the applied temperature relative to an initial surface temperature (i.e. a sequence of taps) prior to implementing the above described method of using two separate user inputs to initiate and set the desired change in an operating parameter.

A user's perception of temperature applied to their skin may exhibit a lag time between when a stimulus is applied to their skin and when that sensation is perceived by the user. Additionally, a user's ability to indicate that a desired thermal stimulus has been applied is also limited by a user's reaction time. Accordingly, in some instances, a user may provide an input to a controller of a device that a desired temperature has been applied at a time point that is after a time when the desired temperature was applied to the user's skin. Thus, in one embodiment, to help provide a desired thermal stimulus to a user, when a setpoint temperature of a thermal profile, such as an average, maximum, and/or minimum operating temperature for a thermal profile, is being set dynamically during a ramp portion of a thermal profile based on user input, the setpoint temperature may be set based on the device temperature applied to an adjacent surface, i.e. a user's skin, at some predetermined time period prior to a controller of the device receiving the input from the user. Appropriate time periods for determining a desired setpoint temperature may be between or equal to 0.1 sec and 1 sec, 0.2 sec and 0.8 sec, 0.3 sec and 0.6 sec, and/or any other appropriate time period. Of course embodiments in which one or more setpoint temperatures of a thermal profile are set based on the actual time of input, and/or are based on a temperature of the device at some time period after the user input, are also contemplated as the disclosure is not so limited.

In some instances it may be desirable to set one or more operating parameters of a device based on a setpoint temperature of the device such as an average temperature, a maximum temperature, and/or a minimum temperature of a thermal profile applied by the device. For example, more aggressive temperatures that provide larger sensation, i.e. larger magnitude temperature differences relative to an initial surface temperature of a surface the device is in contact with, may be indicative of a user desiring more thermal stimulation. Accordingly, when setting an operating temperature of a device, one or more operating parameters of the device may be adjusted based on the selected operating temperature. Specifically, setting an operating temperature of the device at a first magnitude difference relative to an initial surface temperature may cause a controller of the device to set a faster frequency, larger rate of temperature change, larger operating window (i.e. the difference between a maximum and minimum temperature during cyclic operation), longer operation duration, different waveforms, and/or combinations of the forgoing as compared to when the operating temperature is set at a second lower magnitude difference relative to the initial surface temperature. However, while specific relations between a setpoint temperature of the device and the different operating parameters has been described, it should be understood that these various operating parameters may be set individually and/or may have different relationships based on a setpoint temperature of the device as the disclosure is not so limited.

While the above embodiments describe various ways of setting and changing operating parameters of a device, it should be understood that the current disclosure is not limited to only the described embodiments. Instead, it should be understood that the operating parameters of a device may be set and/or altered in any appropriate manner as the disclosure is not so limited. Additionally, while the various methods have been described in a particular order, it should be understood that the various steps of these methods may be performed in any appropriate order.

In some embodiments, the controller may be configured to adjust various parameters based on external metrics. For example, in certain embodiments, the controller is configured adjust the alternating thermal profile portion(s) (e.g., change one or more of the average frequency, average oscillation window, and average temperature) in response to a signal from a sensor in communication with the controller. Non-limiting examples of suitable sensors for use with the devices and methods described herein include temperature sensors (e.g., monitoring skin temperature, ambient temperature, temperature of a heatsink or other thermal apparatus), physiological/biometric sensors (e.g., heart rate, heart rate variability, electrodermal activity, brain/neuronal activity), accelerometers (e.g., for measuring breathing rate, activity levels, sleeping behavior/patterns), and environmental sensors (e.g., humidity, ambient air temperature, light, air flow). In some embodiments, the controlled adjusts the alternating thermal profile in response to an input from the user and/or a signal from the sensor.

In some embodiments, the controller may include one or more proportional, integral, and/or derivative (PID) feed-forward and/or feedback loops to adjust the thermal profile (e.g., in response to one or more sensors in communication with the controller).

A controller for a device used to control the temperature of a surface as described herein may be implemented by any suitable type of analog and/or digital circuitry. For example, the controller may be implemented using hardware or a combination of hardware and software. When implemented using software, suitable software code can be executed on any suitable processor (e.g., a microprocessor) or collection of processors. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments described herein comprises at least one computer-readable storage medium (e.g., RAM, ROM, EEPROM, flash memory or other memory technology, or other tangible, non-transitory computer-readable storage medium) encoded with a computer program (i.e., a plurality of executable instructions) that, when executed on one or more processors, performs the above-discussed functions of one or more embodiments. In addition, it should be appreciated that the reference to a computer program which, when executed, performs any of the above-discussed functions, is not limited to an application program running on a host computer. Rather, the terms computer program and software are used herein in a generic sense to reference any type of computer code (e.g., application software, firmware, microcode, or any other form of computer instruction) that can be employed to program one or more processors to implement aspects of the techniques discussed herein.

In some embodiments, the device may operate in a heating mode. That is to say, in some embodiments, the average temperature of one or more portions of the thermal profile may be greater than the initial temperature (e.g., the temperature of the surface immediately prior to generating the thermal profile). Alternatively, in certain embodiments, the device may operate in a cooling mode. That is to say, in some embodiments, the average temperature of one or more portions of the thermal profile may be less than the initial temperature.

As noted above, existing HVAC systems generally require substantial amounts of energy to heat or cool a commercial building. Embodiments of the present disclosure are estimated to significantly reduce energy consumption related to HVAC usage. For example, outfitting a 1,000 person office building with devices as described herein may consume only 5 kWh a day, as compared to 200 kWh which may be required to adjust a particular region of the building by 1° C. Moreover, methods and devices described herein may provide a user with personal control over his/her level of thermal comfort. By providing a more localized manner of control over a person's thermal comfort, office buildings are estimated to be able to save up to 40% of their HVAC energy usage through a generally reduced HVAC load.

In some embodiments, the ramp profile portion of a thermal profile may include an (initial) temperature adjustment at a region of the heating and/or cooling element(s) (or suitable thermal adjustment apparatus) adjacent the surface from a first (initial) temperature to a second temperature. For example, in some embodiments, the ramp profile portion of a thermal profile comprises adjusting the temperature of the surface from an initial temperature, $T_{surface}$, to a second (setpoint) temperature that may be equal to $T_{avg}+(T_{ow}/2)$ of the alternating thermal profile. In another embodiment, the ramp profile portion of a thermal profile comprises adjusting the temperature of the surface from an initial temperature, $T_{surface}$, to a second (setpoint) temperature that may be equal to $T_{avg}-(T_{ow}/2)$ of the alternating thermal profile. In another embodiment, the ramp profile portion of a thermal profile comprises adjusting the temperature of the surface from an initial temperature, $T_{surface}$, to a second (setpoint) temperature that is equal to $T_{avg}$ of the alternating thermal profile. For some embodiments, the temperature adjustment of the ramp profile portion involves a heating step. In certain embodiments, the temperature adjustment involves a cooling step. The temperature adjustment of the ramp profile may be characterized by an average rate of between 0.1° C./sec and 10.0° C./sec.

In the above embodiment, a thermal profile of a device is described where the temperature cyclically varies between a first temperature with a first larger magnitude relative to an initial surface temperature and a second temperature with a second smaller magnitude relative to the initial surface temperature. Further the described embodiment above included temperature changes during both the increasing and decreasing portions of each temperature cycle that are equal in magnitude, duration, and rate of change. This leads to the temperature increasing and decreasing by an amount equal to half the oscillation window temperature. However, the disclosure is not so limited. For example, depending on the particular embodiment, the different portions of an individual temperature cycle between the first and second temperatures may have different durations, rates of change, and overall profile shape including non-linear thermal profiles and dwell times at particular temperatures. Accordingly, this may result in embodiments where an average temperature is not equal to the average of the first and second temperatures. Therefore, it should be understood that the current disclosure is not limited to any particular thermal profile shape and/or relationship between the various operating parameters of the thermal profile.

The ramp profile portion itself may, in some cases, include a number of portions/regimes.

As discussed herein, a controller may be configured to apply an electrical signal to the heating and/or cooling element(s), for creating a preferred temperature profile at the surface of the heating and/or cooling elements and, hence, the skin. The corresponding electrical signal (i.e., amount of voltage applied over particular period of time, which may generate any suitable thermal profile and is not limited by those specifically shown in the figures) that may be applied from the controller to the corresponding heating and/or cooling element, variations of which will be discussed in more detail below.

In some embodiments, the device (e.g., controller in electrical communication with heating and/or cooling element(s)) may be configured to generate a heating profile that gives rise to a perceived heating experience for the user. That is, the user may feel the sensation of being heated (e.g., locally heated at the surface to which the ramp profile portion of the thermal profile is applied, or at other regions of the body), while the actual temperature of the body is generally maintained. Conversely, for some embodiments, the device may be configured to generate a cooling profile for inducing a perceived cooling effect to the user. Here, similar to the heating experience, the user may feel the sensation of being cooled locally or in other areas of the body, while the actual temperature of the body is generally maintained. The cooling profile may involve a decrease in temperature at the surface of the skin of the user (e.g., during the ramp profile portion of the thermal profile), quickly followed by an increase in temperature (e.g., at the beginning of the (first) alternative profile).

Additional profiles and methods for generating such profiles are generally described in co-owned U.S. Patent Publication Number 2015/0101788, entitled "Methods And Apparatuses For Manipulating Temperature", filed Nov. 24, 2014 and in International Patent Publication Number 2016/0149117, entitled "Methods And Apparatuses For Manipulating Temperature", filed Mar. 11, 2016, each of which is incorporated herein by reference in its entirety.

The temperature at a surface may fall within any appropriate range. For example, the first temperature $T_{surface}$ may be room temperature (e.g., ambient temperature), or normothermia (e.g., resting skin temperature). In some embodiments, the first temperature $T_{surface}$ is greater than or equal to 0° C., greater than or equal to 5° C., greater than or equal to 10° C., greater than or equal to 15° C., greater than or equal to 20° C., greater than or equal to 22° C., greater than or equal to 23° C., greater than or equal to 24° C., greater than or equal to 25° C., greater than or equal to 27° C., greater than or equal to 29° C., greater than or equal to 30° C., greater than or equal to 32° C., greater than or equal to 34° C., greater than or equal to 35° C., greater than or equal to 36° C., greater than or equal to 37° C., greater than or equal to 38° C., or greater than or equal to 40° C. In some embodiments, the first temperature $T_{surface}$ is less than 45° C., less than 40° C., less than 38° C., less than 37° C., less than 36° C., less than 35° C., less than 34° C., less than 32° C., less than 30° C., less than 29° C., less than 27° C., less than 25° C., less than 24° C., less than 23° C., less than 22° C., less than 20° C., less than 15° C., less than 10° C., or less than 5° C. Combinations of the above referenced ranges are also possible (e.g., greater than or equal to 22° C. and less than 29° C., greater than or equal to 34° C. and less than 38° C.). Other temperatures and ranges are also possible.

In some embodiments, the average temperature, $T_{avg}$, during the alternating temperature profile may be greater than or equal to 15° C., greater than or equal to 20° C., greater than or equal to 25° C., greater than or equal to 30° C., greater than or equal to 35° C., greater than or equal to 40° C., or greater than or equal to 45° C. In certain embodiments, the average temperature, $T_{avg}$, during the alternating temperature profile may be less than or equal to 50° C., less than or equal to 45° C., less than or equal to 40° C., less than or equal to 35° C., less than or equal to 30° C., less than or equal to 25° C., or less than or equal to 20° C. Combinations of the above referenced ranges are also possible (e.g., greater than or equal to 15° C. and less than or equal to 50° C., greater than or equal to 20° C. and less than or equal to 45° C., greater than or equal to 25° C. and less than or equal to 45° C.). Other ranges are also possible. It can be appreciated that the device may adjust the temperature at the surface of the skin so as to change during various portions of a thermal profile, according to a preferred shape or profile. For example, at any given time during the thermal profile, the temperature change may exhibit a behavior that is substantially linear, non-linear, exponential (e.g., exponential growth, exponential decay), polynomial (quadratic, cubed, etc.), irregular (e.g., following a piecewise function), sinusoidal, or another suitable behavior.

In some embodiments, the thermal adjustment apparatus, or controller configured to apply an electrical signal to the heating and/or cooling element(s), may generate a ramp profile portion over a time period of less than or equal to 120 seconds. In certain embodiments, the time period of an entire ramp profile portion from an initial temperature to a second (setpoint) temperature (e.g. a temperature of $T_{avg} \pm (T_{ow}/2)$) before beginning an alternating thermal profile portion is less than or equal to 90 seconds, less than or equal to 75 seconds, less than or equal to 60 seconds, less than or equal to 50 seconds, less than or equal to 45 seconds, less than or equal to 40 seconds, less than or equal to 30 seconds, less than or equal to 20 seconds, less than or equal to 15 seconds, less than or equal to 10 seconds, less than or equal to 7 seconds, less than or equal to 5 seconds, less than or equal to 4 seconds, less than or equal to 3 seconds, less than or equal to 2 seconds, or less than or equal to 1 second. In some embodiments, the time period of a ramp profile portion is greater than 2 seconds, greater than 3 seconds, greater than 4 seconds, greater than 5 seconds, greater than 6 seconds, greater than 7 seconds, greater than 10 seconds, greater than 15 seconds, greater than 20 seconds, greater than 30 seconds, greater than 40 seconds, greater than 50 seconds, greater than 60 seconds, greater than 75 seconds, or greater than 90 seconds. Combinations of the above-referenced ranges are also possible (e.g., between 2 seconds and 5 seconds, between 3 seconds and 10 seconds, between 10 seconds and 30 seconds, between 10 seconds and 60 seconds, or between 15 seconds and 90 seconds). Other ranges are also possible.

Figure 3A:
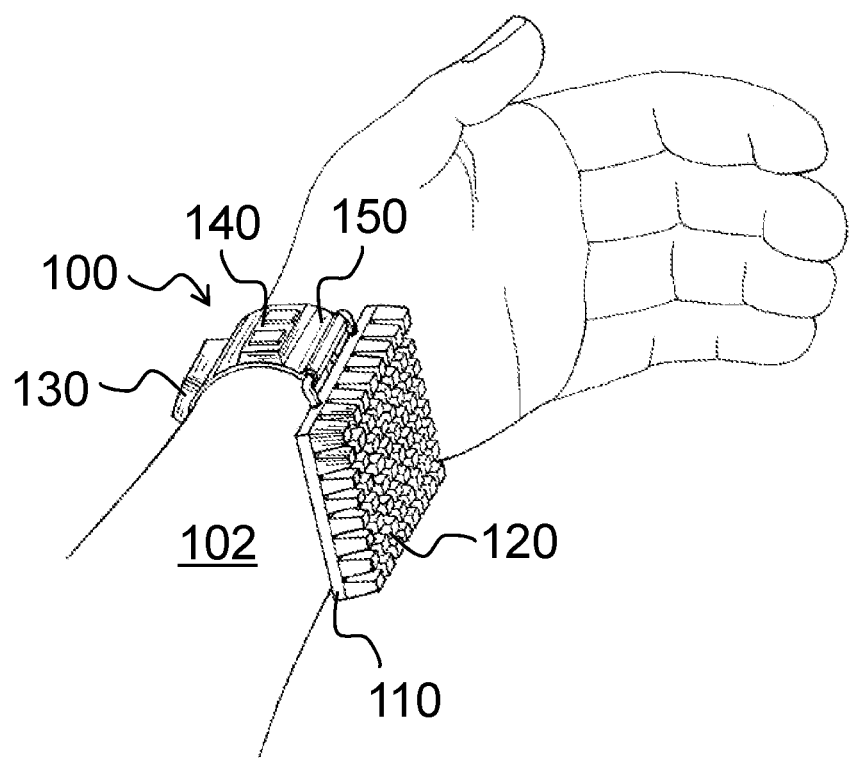
FIG. 3A shows a perspective view of an exemplary device for manipulating the temperature of a surface worn by a user according to one set of embodiments.
Figure 3B:
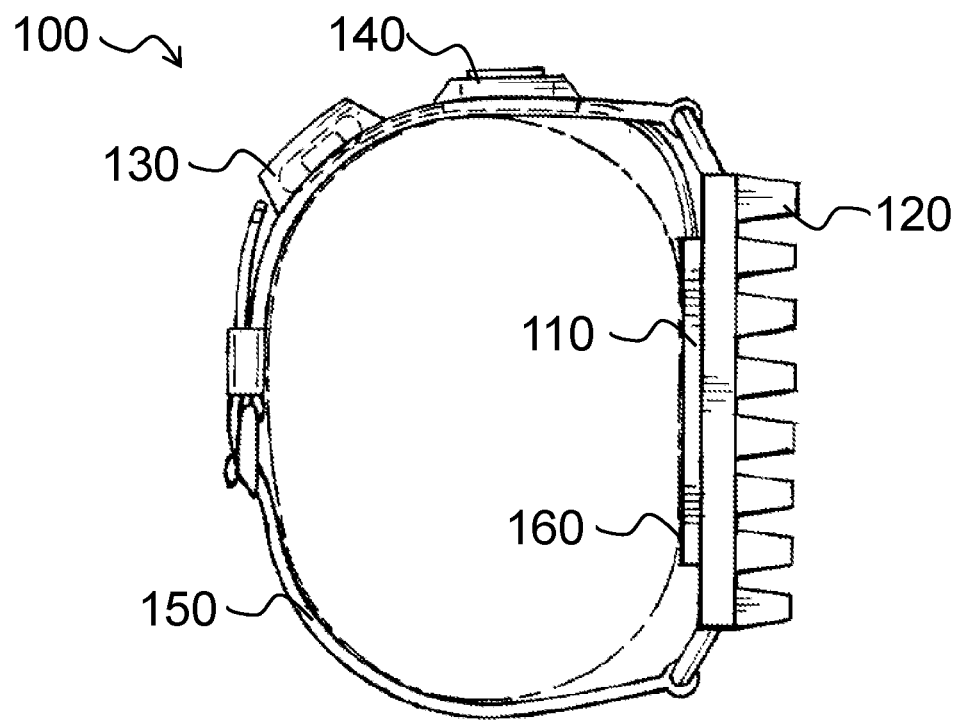
FIG. 3B shows a side view of an exemplary device for manipulating the temperature of a surface worn by a user according to one set of embodiments.
Figure 3C:
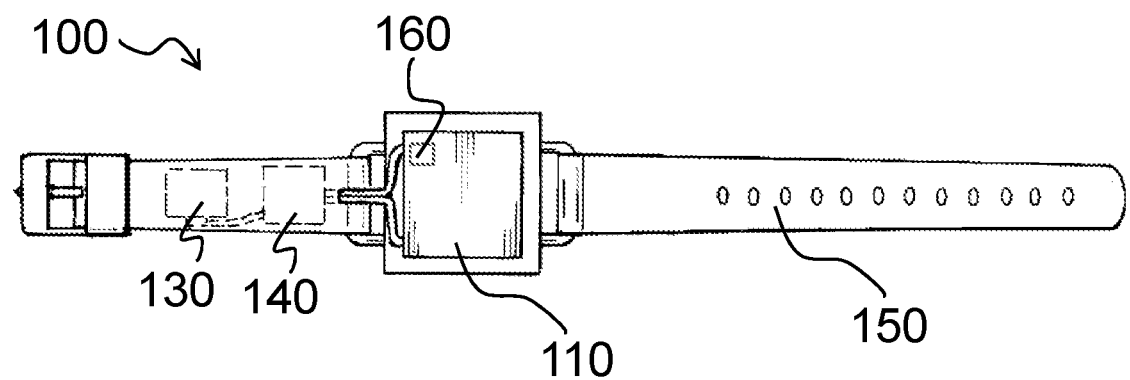
FIG. 3C shows a top-down view of an exemplary device for manipulating the temperature of a surface worn by a user according to one set of embodiments.

FIGS. 3A-3C depict an embodiment of a device 100 that includes a heating and/or cooling element 110 that, during use, is configured to be positioned adjacent to the surface of the user's skin 102. As explained further below, the device may include multiple heating and/or cooling elements (e.g., thermoelectric materials, resistive heaters, and combinations thereof) positioned at the surface of the skin. The device 100 may optionally include a heating and/or cooling element 120 (e.g., heat sink) located on the side of the device opposite the skin in a manner that covers the heating and/or cooling element 110.

The heating and/or cooling element 120, described further below, may dissipate heat to and/or from the heating and/or cooling element(s), as desired. The heating and/or cooling element such as a thermoelectric material may include any suitable material, such as metal (e.g., aluminum, copper, stainless steel, etc.), thermally conductive polymer, porous ceramic, or another appropriate material.

The device may include a power source 130 (e.g., battery, plug-in outlet, etc.) and a controller 140, for applying appropriate electrical signals to the heating and/or cooling element, for manipulating the temperature at the surface (e.g., of the skin). In some cases, the controller may have, one or more inputs and/or outputs to accommodate user control of the device in a suitable and convenient manner. It should be understood that any appropriate input may be used as the disclosure is not so limited. For example, one or more buttons, a keypad, touch pad, or other appropriate component may be integrated with a device to accept user inputs. Alternatively, an inertial monitoring unit (IMU) may be used to recognize one or more gestures from a user to function as an input. In yet another embodiment, a microphone may be integrated with a thermal device that permits the controller of the thermal device to accept voice commands. Additionally, in some embodiments, a separate computing device in either wireless, or wired, communication with a controller of a thermal device may be used to input the desired commands. For instance, a smartphone, tablet, or other computing device may have a graphical user interface installed that includes buttons, input fields, and other interface components that permit the user to input one or more commands that may then be transmitted to the controller of the thermal device using an appropriate communication protocol such as blue tooth communication, radio frequency communication, wifi communication, or any other appropriate wireless or wired communication protocol. Accordingly, it should be understood that the currently disclosed devices are not limited to any particular type of input device as the disclosure is not limited in this fashion.

In some embodiments, the device (e.g., as shown in FIGS. 3B-3C) may comprise a sensor 160. In certain embodiments, sensor 160 is positioned adjacent (e.g., directly adjacent) the heating and/or cooling element 110. However, those skilled in the art based upon the teachings of this specification would understand that sensor 160 may be positioned in any suitable location on the device. In certain embodiments, the sensor is not positioned on the device and communicates (e.g., wirelessly) with the controller. In some cases, more than one sensor may be in communication with the device. In some embodiments, at least some of the more than one sensors may be positioned on the device. Each of the elements of the device, i.e., the heating and/or cooling element 110, heating and/or cooling element 120, power source 130, controller 140, and/or sensor 160 may be suitably connected to an appropriate band or other securing member 150 to facilitate attachment to a desired user body part. In some cases, a band 150 may be flexibly adjustable so as to allow for the heating and/or cooling element 110 to be comfortably and suitably positioned against or otherwise adjacent the surface of the skin such that a thermal profile generated by the heating and/or cooling element are effective to provide the user with a preferred thermal sensation. Though, for some embodiments, the band 150 may exhibit relatively rigid mechanical behavior, providing support for the overall device. It can be appreciated that the band 150 may have any suitable structure and, in some cases, may have stylistic aspects which may lend the device to be worn as a bracelet, anklet, necklace, etc. The band may include any suitable material, such as, but not limited to, metal, plastic, rubber, leather, synthetic leather, or combinations thereof.

While the use of a band to retain a thermal device including heating and/or cooling elements adjacent to a desired portion of a user's body is described above, other embodiments are contemplated. Specifically, the disclosed devices may be worn adjacent to any appropriate portion of a user's body including, but not limited to, a head, neck, back, chest, sternum, stomach, arms, legs, hands, feet, and/or any other appropriate body portion. Further, the disclosed devices may be incorporated into any structure capable of maintaining a device adjacent to a desired portion of a user's body. For example, in some embodiments, not shown in the figures, the device may be incorporated into a fabric (e.g., an article of clothing) or rigid structures. Examples of wearable structures the disclosed devices may be incorporated into include, but are not limited to a scarf, necklace, armband, wristband, sleeve, legging, shirt, shorts, pants, vest, rigid structures attachable to a body portion, or any other wearable article that the disclosed devices may be incorporated with. The size of the disclosed devices may be selected, in some embodiments, such that the device fits comfortably on a wrist, on an ankle, within an article of clothing, within the palm of a user's hand, etc. However, embodiments in which a device has a size both smaller or larger than those noted above are also contemplated as the disclosure is not so limited.

It can be appreciated that while the heating and/or cooling element(s) may be positioned directly adjacent to a surface of the user's skin, in accordance with aspects of the present disclosure, the heating and/or cooling element(s) are not required to be in direct contact with the user's skin; for example, an additional layer (not shown in the figures) may be placed between the heating and/or cooling element(s) and the surface of the skin. For example, a thermally conductive or insulative layer, a protective layer, a support layer (e.g., for added comfort), or another appropriate material.

Figure 3D:
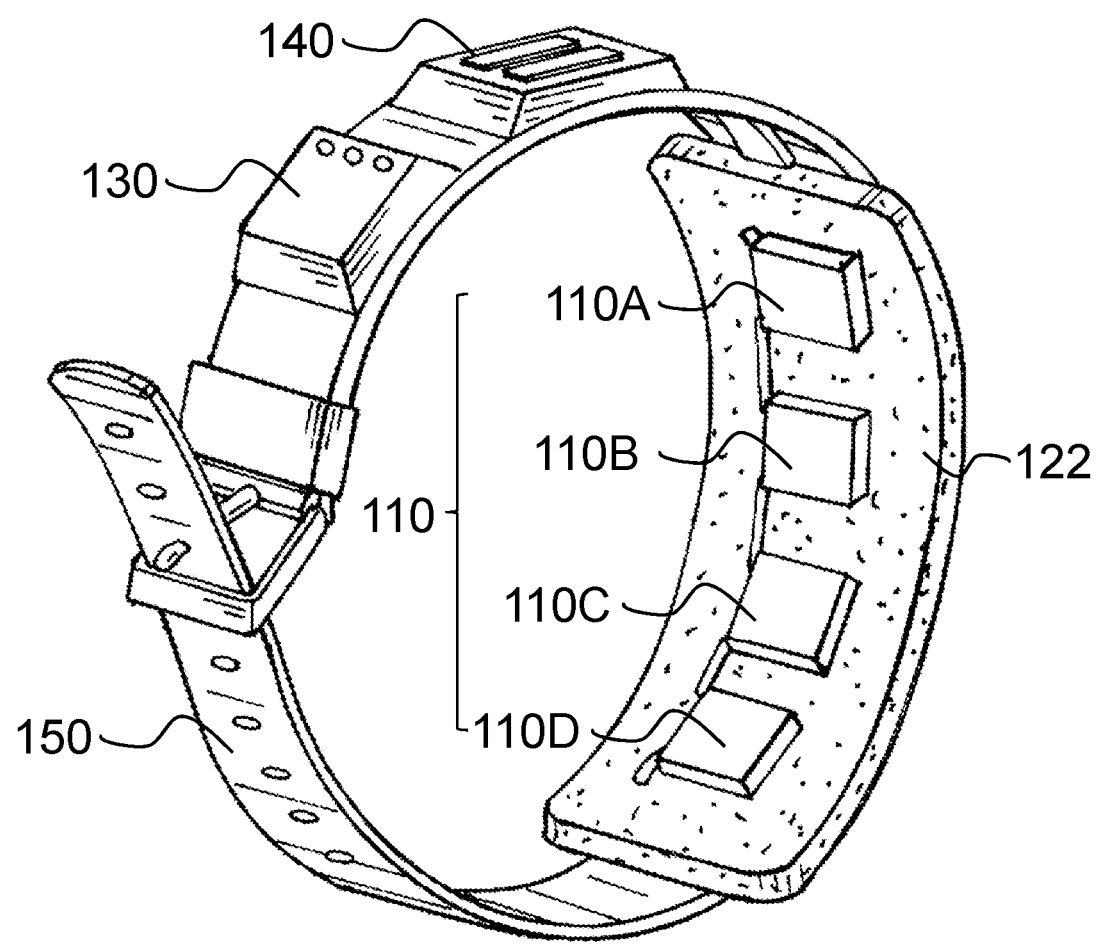
FIG. 3D shows a perspective view of an exemplary device for manipulating the temperature of a surface worn by a user according to one set of embodiments.
Figure 3E:
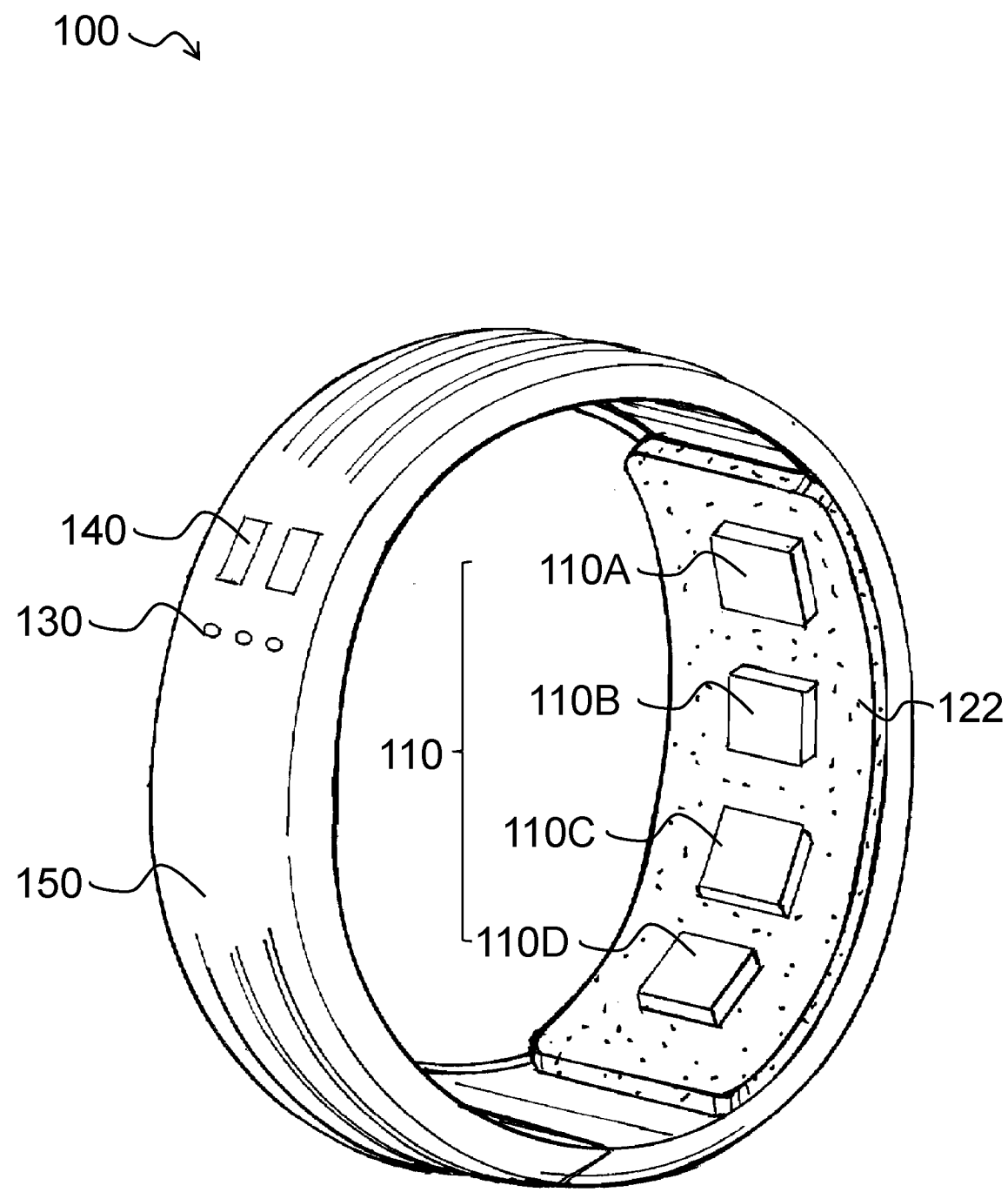
FIG. 3E shows a perspective view of an exemplary device for manipulating the temperature of a surface worn by a user according to one set of embodiments.

FIGS. 3D-3E show embodiments where the device 100 includes a thermally insulative material 122 located on the side of the thermoelectric opposite the skin, covering the thermoelectric material(s). As a result, the thermally insulative material 122 substantially maintains the overall level of heat generated by the heating and/or cooling element(s), located at the surface of the skin. In some cases, as discussed further below, the thermally insulative material enhances the effect of the thermal profile generated by the heating and/or cooling element(s). The thermally insulative material may include any suitable material, for example, polymer, plastic, elastomer (e.g., rubber, neoprene, etc.), and/or another appropriate material. Such insulative materials may also lend themselves to a device that is less bulky and more flexibility than, for example, if a large heat sink were placed over the thermoelectric material(s). Accordingly, covering the heating and/or cooling element(s) with a suitable insulative layer such as neoprene, other rubbers or cloth or textile-based materials may allow the device to be more desirable to wear. For some embodiments, the heating and/or cooling element(s) may be exposed to air, without a covering or other material located thereon.

In some embodiments, the device 100 may include a number of heating and/or cooling elements. For example, as illustrated in FIGS. 3D-3E, rather than a single heating and/or cooling element, the device 100 may include a plurality of smaller heating and/or cooling elements 110A, 110B, 110C, 110D located adjacent to one another. The heating and/or cooling elements 110A, 110B, 110C, 110D of FIGS. 3D-3E may be sized and arranged in a manner so as to accommodate flexing of the device, for example, around a wrist or other part of the body. Similar to a watch having small rigid components (e.g., metallic parts) that are mutually connected, yet able to flex with respect to one another along the wristband, the plurality of heating and/or cooling elements may be relatively small, yet arranged in a manner that allows for flexibility and overall wearability of the wristband 150. Accordingly, the relatively small heating and/or cooling elements may be arranged so as to accommodate the curvature of certain body parts. Thus, the wristband, together with the heating and/or cooling elements may provide the ability for the device to be adjustably and, hence, snugly fit to the user.

The device may include any suitable number of heating and/or cooling elements. For example, the device may include 2 or more, 3 or more, 4 or more, 5 or more, 10 or more, etc. such heating and/or cooling elements. The heating and/or cooling elements may be arranged in any appropriate pattern along the surface of the device, for example, aligned along a row, arranged in a grid-like formation, positioned in an irregular pattern, arranged to form a particular shape (e.g., ellipse, circular, quadrilateral, hexagonal, etc.), or may be configured in another appropriate way. It may be preferable for the heating and/or cooling elements to be located in relatively close proximity to one another, so that the cluster of heating and/or cooling elements is able to generate one or more thermal profiles in a suitable manner, for example, thermal profiles that are more concentrated at the surface, so as to elicit a more pronounced response, than if the heating and/or cooling elements are spaced further apart from one another.

In some cases, the heating and/or cooling elements may be in electrical communication with one another. For example, the heating and/or cooling elements may be arranged so as to have an electrical connection in series with each other. Accordingly, an electrical signal applied to one of the heating and/or cooling elements may also be applied to the others to which it is connected. Or, the heating and/or cooling elements may be electrically isolated from one another, for example, so as to be separately stimulated by a controller, with electrical signals appropriately tailored for each heating and/or cooling element, for example, at preferred times, magnitudes, and/or rates, as desired.

As noted above, the device may include a controller that is in electrical communication with the heating and/or cooling element(s), or other appropriate thermal adjustment apparatus. In some embodiments, the controller is configured to apply a series of electrical signals to the heating and/or cooling element(s) to cause the thermal profile to be generated at a region of the heating and/or cooling element(s) adjacent the surface.

In some embodiments, as noted above, the controller may be in separate electrical communication with each of several heating and/or cooling elements. As a result, the controller may be configured to cause two or more heating and/or cooling elements to generate two or more thermal profiles, respectively, that are separate and distinct from one another; for example, a first heating and/or cooling element generating a first thermal profile and a second heating and/or cooling element generating a second thermal profile. It can be appreciated that various characteristics of the respective thermal profiles may be the same or different. In some embodiments, respective thermal profiles may be generated in a substantially simultaneous manner. Alternatively, for certain embodiments, the first thermal profile and the second thermal profile may be generated at different times. Or, as described above, the controller may be configured to cause the heating and/or cooling element(s) to generate a plurality of respective thermal profiles in succession, in any suitable pattern.

As discussed above, the thermal adjustment apparatus may include a controller that applies an appropriate electrical signal to the heating and/or cooling element(s) (e.g., thermoelectric materials, resistive heaters), for generating the appropriate thermal profiles(s). The electrical signal may include a suitable step up/down in voltage, current, etc.

In some embodiments, the controller includes a voltage source, for generating a suitable electrical signal. In certain embodiments, the voltage source applies a voltage to the heating and/or cooling element(s) suitable to create a thermal profile at the surface of the skin of a user. It can be appreciated that voltages may be applied in accordance with any appropriate signal pattern. For instance, rather than applying a constant voltage, the electrical signal may employ pulse width modulation, where the width of a given thermal pulse is modulated according to a suitable duty cycle (e.g., 10-50% duty cycle), for example, for modulating (and conserving) the power provided to the device. In some cases, pulse width modulation may be applied using suitable duty cycles having relatively short timescales (>100 Hz). Any suitable form of pulse width modulation may be employed.

In some cases, whether the potential that is applied is positive or negative may correspond to whether a heating profile or cooling profile is desired. Though, it can be appreciated that certain heating or cooling profile may involve both positive and negative voltages being applied to the heating and/or cooling element(s) (e.g., via pulse width modulation where voltages are pulsed at an appropriate duty cycle). The effective average magnitude of a voltage applied to the heating and/or cooling element(s) at any given point may fall within a suitable range. For example, the average magnitude of the voltage applied to the heating and/or cooling element(s) may be between 0.001 to 0.01 V, between 0.01 to 0.1 V, between 0.1 V and 10.0 V, between 1.0 V and 8.0 V, between 2.0 V and 5.0 V, between 0.1 V and 5.0 V, between 0.1 V and 1.5 V, between 0.1 V and 1.0 V, between 1.0 V and 3.0 V, between 3.0 V and 8.0 V, or any other appropriate range.

In some embodiments, the controller includes a current source, for generating a suitable electrical signal. The current source may apply a current to the heating and/or cooling element(s), for generating a thermal profile at the surface of the skin of a user. The magnitude of a current applied to the heating and/or cooling element(s) at any given point may fall within a suitable range. In some embodiments, the magnitude of a current applied to the thermoelectric material(s) may be between 0.001 A and 0.01 A, between 0.01 and 0.1 A, between 0.1 A and 4.0 A, between 0.1 A and 3.5 A, between 0.1 A and 3.0 A, between 0.2 A and 2.5 A, between 0.5 A and 2.0 A, between 1.0 A and 2.0 A, between 0.1 A and 1.5 A, between 0.1 A and 1.0 A, between 0.5 A and 1.0 A, between 0.1 A and 0.5 A, between 1.0 A and 1.5 A, or any other appropriate range. The electrical signal(s) may be applied to the heating and/or cooling element(s) in accordance with any suitable form or pattern. In some embodiments, the electrical signal(s) may be applied to the heating and/or cooling element(s) as one or more square waves (i.e., a constant voltage/current applied for a period of time), which may result in a particular rate of temperature change, average frequency, average oscillation window, and/or average temperature, depending on how the electrical signal is applied. Or, the electrical signal(s) may exhibit more complex behavior, for example, the electrical signal(s) may be applied as a linear ramp function, non-linear, exponential, polynomial function, sinusoidal function, piecewise function, etc.

In certain embodiments, the controller may apply an electrical signal to the heating and/or cooling element(s) as dictated by a Proportional, Integral, and/or Derivative feedback loop receiving information the temperature of the surface from a temperature sensor embedded in the heating and cooling system. Those skilled in the art would be capable of implementing and tuning the PID control system for the controlled generation of temperature profiles on the surface.

In certain embodiments, the controller may apply an electrical signal to the heating and/or cooling element(s) according to a suitable duty cycle. The term duty cycle as known in the art generally refers to the percentage of a time period in which an electrical signal is active. In various embodiments, the electrical signal applied to the heating and/or cooling element(s) by the controller may exhibit a duty cycle of between 10% and 50%, greater than or equal to 10%, greater than or equal to 20%, greater than or equal to 30%, greater than or equal to 40%, or greater than or equal to 50%. In some embodiments, the duty cycle applied by the controller may be less than 50%, less than 40%, less than 30%, less than 20%, or less than 10%. Combinations of the above referenced ranges are also possible (e.g., between 10% and 50%).

As will be understood by those skilled in the art, the particular ranges of electrical signal (i.e., voltages, currents) are non-limiting and may suitably vary depending, in part, on the overall configuration of the device, particular materials selected (e.g., thermoelectric materials, number of thermoelectric materials, resistive heaters, number of resistive heaters), intrinsic resistances of various components within the device, or other aspects that may contribute to the functionality of the device.

As noted above, the heating and/or cooling element of the device may include one or more thermoelectric materials. Non-limiting examples of suitable thermoelectric materials may include columns of p-type and n-type doped semiconductor materials, bismuth chalcogenides (e.g., $Bi_2Te_3$, $Bi_2Se_3$), lead selenide, Si—Ge alloys, skutterudites (e.g., including the formula $LM_4X_{12}$, wherein L is a rare earth metal, M is a transition metal, and X is a metalloid), or any other suitable thermoelectric materials.

The heating and/or cooling elements such as thermoelectric material(s) may have any suitable thickness. For example, in some embodiments, the thickness may be selected such that the heating and/or cooling element(s) may be comfortably held against the wrist, arm, leg, ankle, neck, or any other suitable part of the body. In some embodiments, the thickness of each of the heating and/or cooling elements may be between 0.1 millimeter and 5 millimeters (e.g., between 0.1 millimeter and 3 millimeters, between 0.5 millimeters and 1 millimeter). Other thicknesses are also possible.

In some embodiments, each of the thermoelectric materials, or modules that include the heating and/or cooling element(s), may have a largest average cross-sectional dimension of between 5 mm and 4 cm (e.g., between 30 mm and 500 mm). Other average cross-sectional dimensions are also possible. Those skilled in the art would be capable of selecting an appropriate size for the heating and/or cooling element(s) based upon the configuration of the device.

Heating and/or cooling elements, or modules thereof, may be provided in any suitable configuration. For example, a module may include thermoelectric materials sandwiched between ceramic plates, in some cases, for protection and support, as well as to provide thermal conductivity to the surface of the skin.

For certain embodiments, the device may incorporate a thermally conductive material, for example, for thermal dissipation of the generated heating or cooling. For example, it may be desirable to switch rapidly between heating and cooling modes. Accordingly, the ability to dissipate heat may allow for residual heating or cooling to be reduced.

Any suitable dissipation unit may be employed, for example, a heat sink, a fan, a phase change material, a heat exchanger, or combinations thereof. In some embodiments, the thermal dissipation unit has a size and/or weight such that it can be mounted comfortably on the device and, in turn, for example, on a wrist of a user. Additionally, in some embodiments, the dissipation unit may be integrated with one or more portions of the overall heating and/or cooling device, including for example, a thermally conductive housing of the device that is thermally coupled to the heating and/or cooling elements. However, it should be understood that any appropriate type of dissipation unit may be used as the disclosure is not limited in this fashion.

As described above, in some embodiments, the device includes a suitable power source. The power source may include any appropriate materials, such as one or more batteries, photovoltaic cells, etc. Non-limiting examples of suitable batteries include Li-polymer (e.g., with between 100 and 1000 mAh of battery life), Li-ion, nickel cadmium, nickel metal hydride, or the like. In some cases, the battery may output a constant voltage and the controller may be configured to apply an appropriate degree of pulse-width modulation to generate time-varying voltage profiles.

The device may be further configured to use relatively low amounts of power, in contrast with HVAC systems or other localized electronic thermal sources such as heaters, fans, or the like.

In certain embodiments, and as described above, the device may include one or more sensors arranged to collect information at the region of the heating and/or cooling element(s) adjacent the surface. Any suitable sensor(s) may be employed, for example, temperature sensors (e.g., thermistors, thermocouples), humidity and/or moisture sensors, barometers, etc., in any appropriate configuration. In some embodiments, the device includes one or more temperature sensors for monitoring the temperature at the surface of the heating and/or cooling element(s) and/or skin. For example, if the temperature measured at the surface of the heating and/or cooling element(s) and/or skin exceeds or is lower than a desired temperature, the sensor may send a signal to the controller to adjust the applied electrical signal (e.g., apply a negative (or lower) voltage to reduce the temperature, apply a positive (or higher) voltage to increase the temperature) to result in a preferred thermal profile.

In some embodiments, the temperature sensor may be incorporated with the controller, for monitoring the temperature of the controller. In certain embodiments, one or more temperature sensors may be placed directly adjacent one or more surfaces of the heating and/or cooling element (s). In some embodiments, the temperature sensor(s) may be arranged for sensing the temperature of ambient air. In some embodiments, the temperature sensor(s) may measure the temperature difference across different components of the device (e.g., between the surface of the skin and the heating and/or cooling element(s), between the heating and/or cooling element(s) and ambient air). The temperature sensor(s), in some embodiments, may be configured with the controller to operate in accordance with a feedback loop, for example, to prevent excessive heating or cooling of the device and/or to maintain the temperature at the surface within a preferred range.

The device may include additional control features, as desired, for example, wireless capabilities for enabling suitable communication with other devices/systems (e.g., for controlling aspects of the device, controlling/monitoring the temperature at the surface of the skin, etc.). Wireless devices are generally known in the art and may include, in some cases, wifi and/or Bluetooth systems.

Additional non-limiting examples of devices and methods for manipulating the temperature of a surface are described in more detail in commonly-owned U.S. Patent Publication Number 2015/0101788, entitled "Methods And Apparatuses For Manipulating Temperature", filed Nov. 24, 2014 and in International Patent Publication Number 2016/0149117, entitled "Methods And Apparatuses For Manipulating Temperature", filed Mar. 11, 2016, each of which is incorporated herein by reference in its entirety.

EXAMPLES

Humans are generally hard-wired to respond physiologically and psychologically to thermal sensations, which can improve whole body comfort, influence our experience of social emotions, affect decision making, and influence the balance of the autonomic nervous system. In some cases, a constant temperature set point does not translate to a constant thermal sensation. First, generating thermal sensations must take into account the nuances of how thermoreceptors in the skin translate thermal stimuli into thermal sensations. The skin's response to temperature is dynamic and requires a precise yet dynamic solution. Second, the body's response to thermal sensations generally depends on physiological, thermoregulatory, emotional, and environmental conditions. Unlike conventional heating and cooling, there is not a fixed temperature set point (or even a fixed level of thermal sensation) that is sufficient to achieve the desired effects at any given time. The constantly evolving state of the human body creates a moving target for the desired and necessary level of thermal sensation, which may also be accounted for in an engineering solution.

Figure 4A:
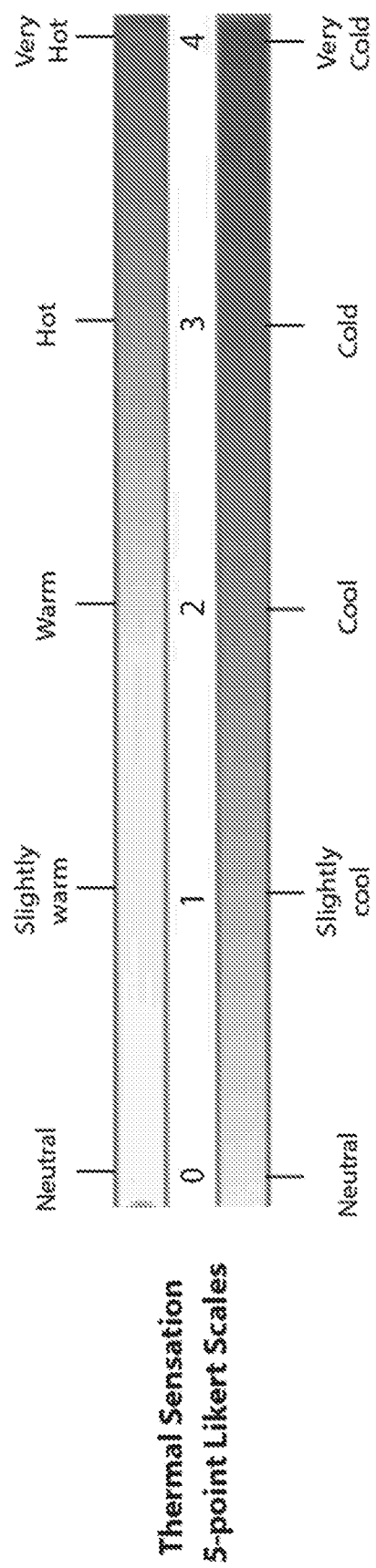
FIG. 4A shows the 5-point Likert scales used for thermal sensation reporting.
Figure 4B:
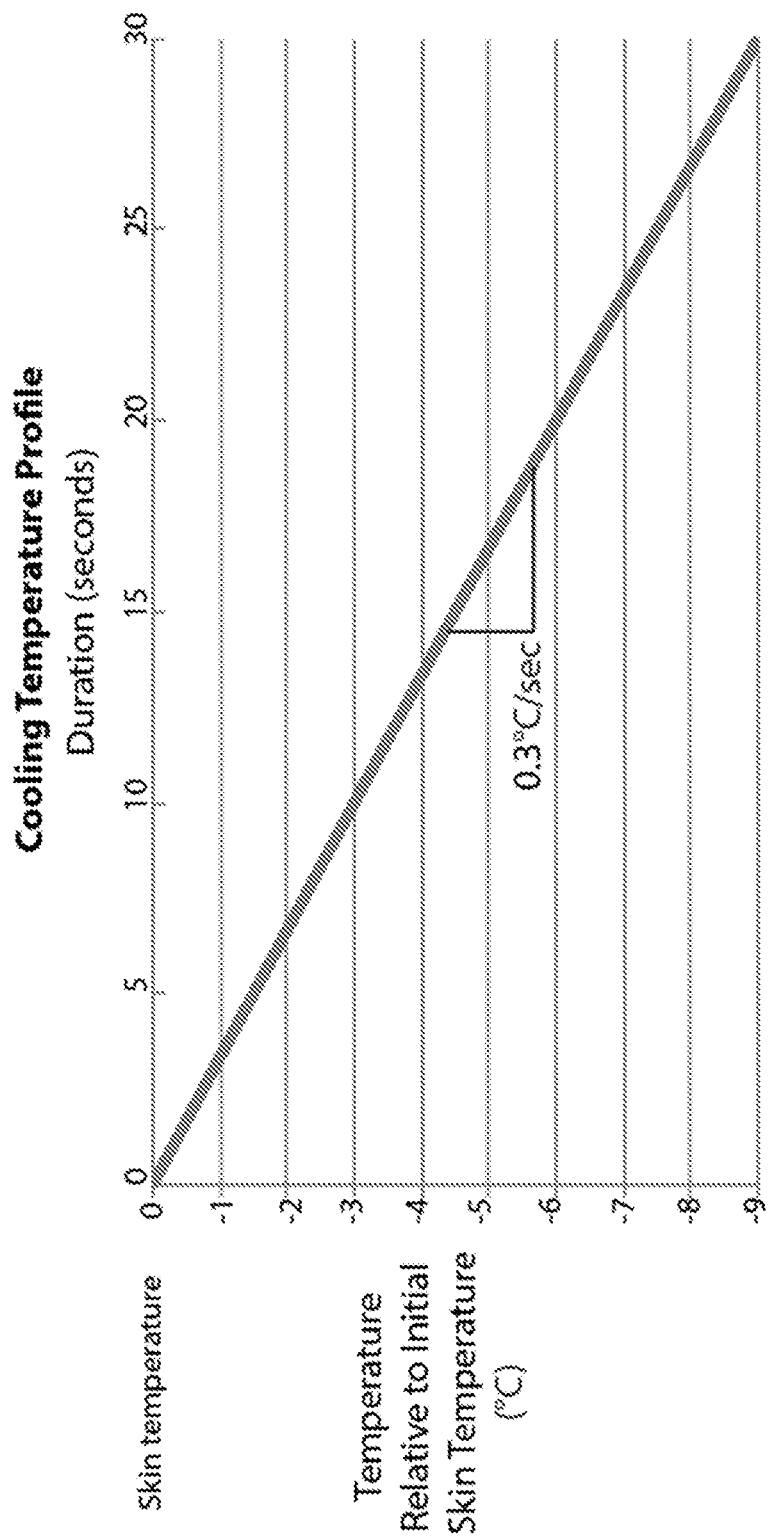
FIG. 4B shows an exemplary plot of the temperature profile used to generate a thermal sensation for 2 individuals on 5 different days, according to one set of embodiments.
Figure 4C:
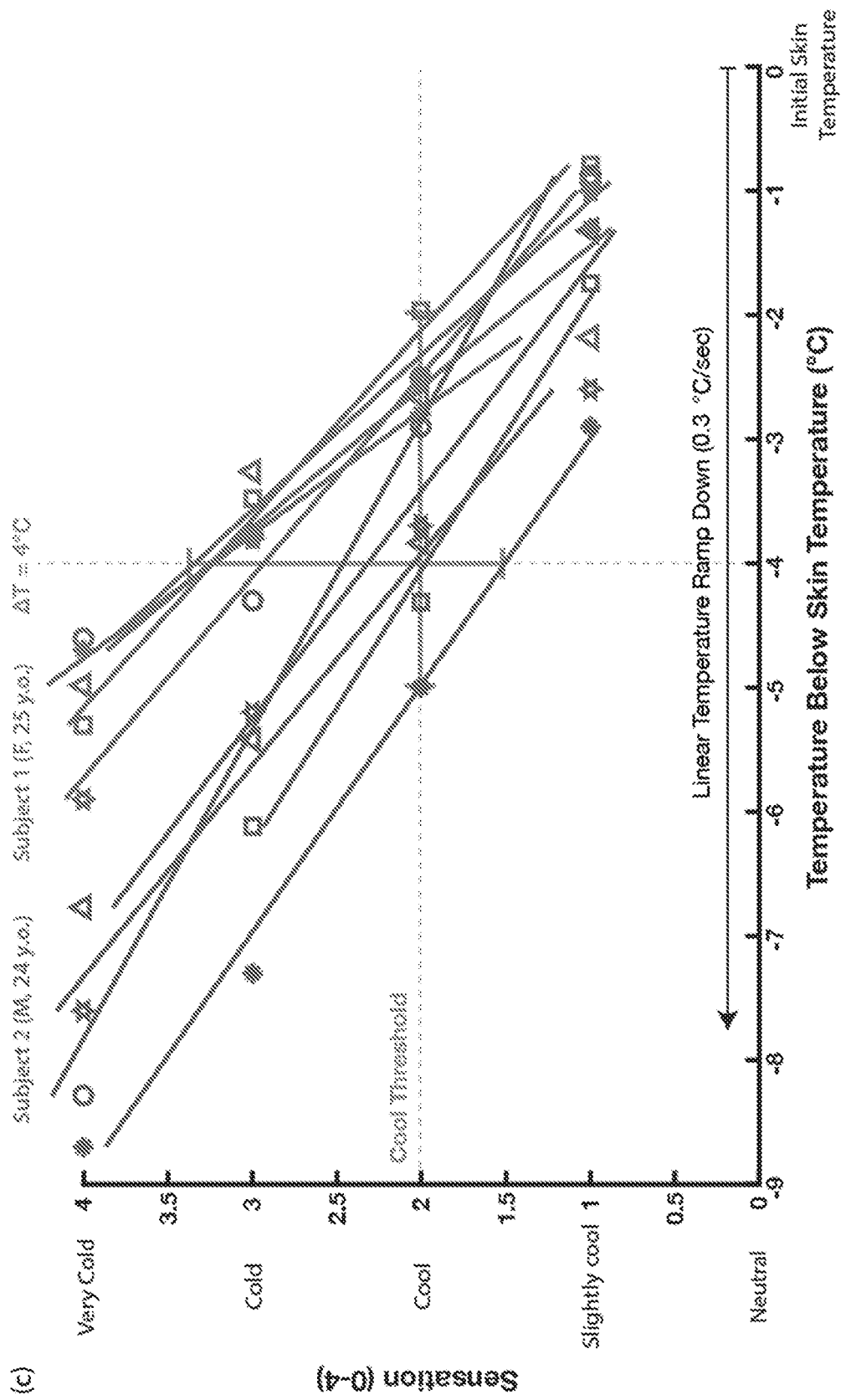
FIG. 4C shows an exemplary plot of the sensation responses of two individual subjects experiencing the identical temperature ramp illustrated in (FIG. 4B) on 5 different days.

FIGS. 4A-4C show the results of thermal sensation trials conducted on 2 different people on 5 different days. To collect real-time sensation data, subjects were provided with a slider mapped onto a 5-point thermal sensation Likert scale (FIG. 4A). The participants were exposed to a controlled thermal sensation from a 6.25 cm$^2$ cooling area positioned on the inside of the wrist and held in place with an adjustable strap. The participant then used their free hand to move the slider as they experienced an evolving thermal sensation. The subjects experienced identical cooling temperature ramps (FIG. 4B), starting at skin temperature and then decreasing at a rate of 0.3 C/sec.

Considering intrapersonal variability, a significant variation in the temperature offset required to achieve a Cool (2) sensation for both Subject 1 and Subject 2 was observed (FIG. 4C). Subject 1 experienced over 1° C. variability in the temperature offset required to generate a cool sensation, whereas Subject 2 exhibited over a 2° C. window in which a sensation was reported as Cool (2). Comparing Subject 1 and Subject 2 to illustrate the magnitude of interpersonal variability, there was over a 3° C. window (from 2° C. to 5° C.) that could generate a cool sensation for a given individual on a given day. Alternatively, FIG. 4C shows that if the temperature offset is fixed at 4° C. below initial skin temperature then the resulting sensation could vary from Slightly Cool to beyond Cold, depending on the individual and the day. These studies illustrate that a predetermined temperature offset may not lead to predictable cooling sensations, even when the temperature rate is controlled for, due to sources of intrapersonal and interpersonal variability.

Figure 5:
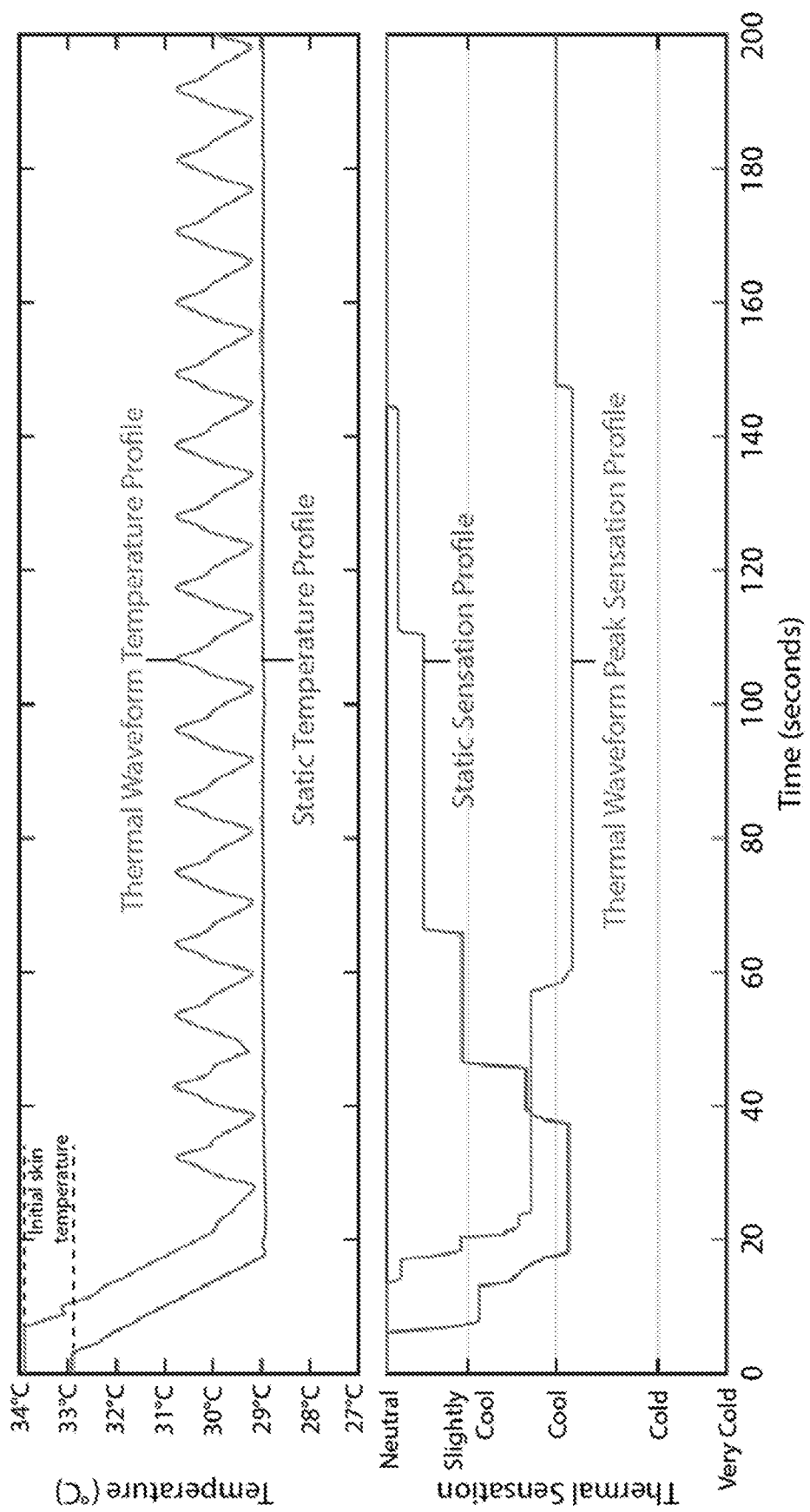
FIG. 5 shows (top) exemplary thermal profiles of a cooling thermal profile and a static thermal profile with the same $\Delta T_{AVG}=4°$ C. relative to initial skin temperature and (bottom) thermal sensations generated by alternating profile and static temperature profile over the first 200 seconds are shown.

When oscillating the temperature within an oscillation window, $\Delta T_{OW}$, it was shown that the ramp up portion of the oscillation creates a noticeable temperature sensation whereas the ramp down portion of the oscillation creates a neutral sensation under most conditions. Therefore by oscillating the temperature in the approach described above, periodic sensations of warming or cooling were created. FIG. 5 compares cooling the skin using an alternating thermal profile to a static temperature profile with the same $\Delta T_{AVG}$ (equivalent to $(T-T_{surface})$ in FIGS. 1A-1E). In both scenarios $\Delta T_{AVG}$=4° C. The profile in FIG. 5 delivered cyclic cooling pulses with $\Delta T_{OW}$=1.6° C. The rate of temperature change was >0.1° C. The reported sensation for the alternating thermal profile and static cooling stimuli over 200 seconds are shown in FIG. 5. Both temperature profiles achieve sensation ratings of Cool (3) during initialization. Due to thermal adaptation, the sensations generated by the static temperature profile begin to decrease within 30 seconds of initialization and become almost unperceivable (below Slightly Cool (1)) within 90 seconds of maintaining skin temperature at 4° C. below $T_{SURFACE}$. The alternating thermal profile, however, creates consistently "cool" thermal sensations over the course of the entire 200 seconds. This example illustrates the ability of alternating thermal profiles to generate consistent sensations over time and to overcome the desensitizing effects of thermal adaptation.

Figure 6:
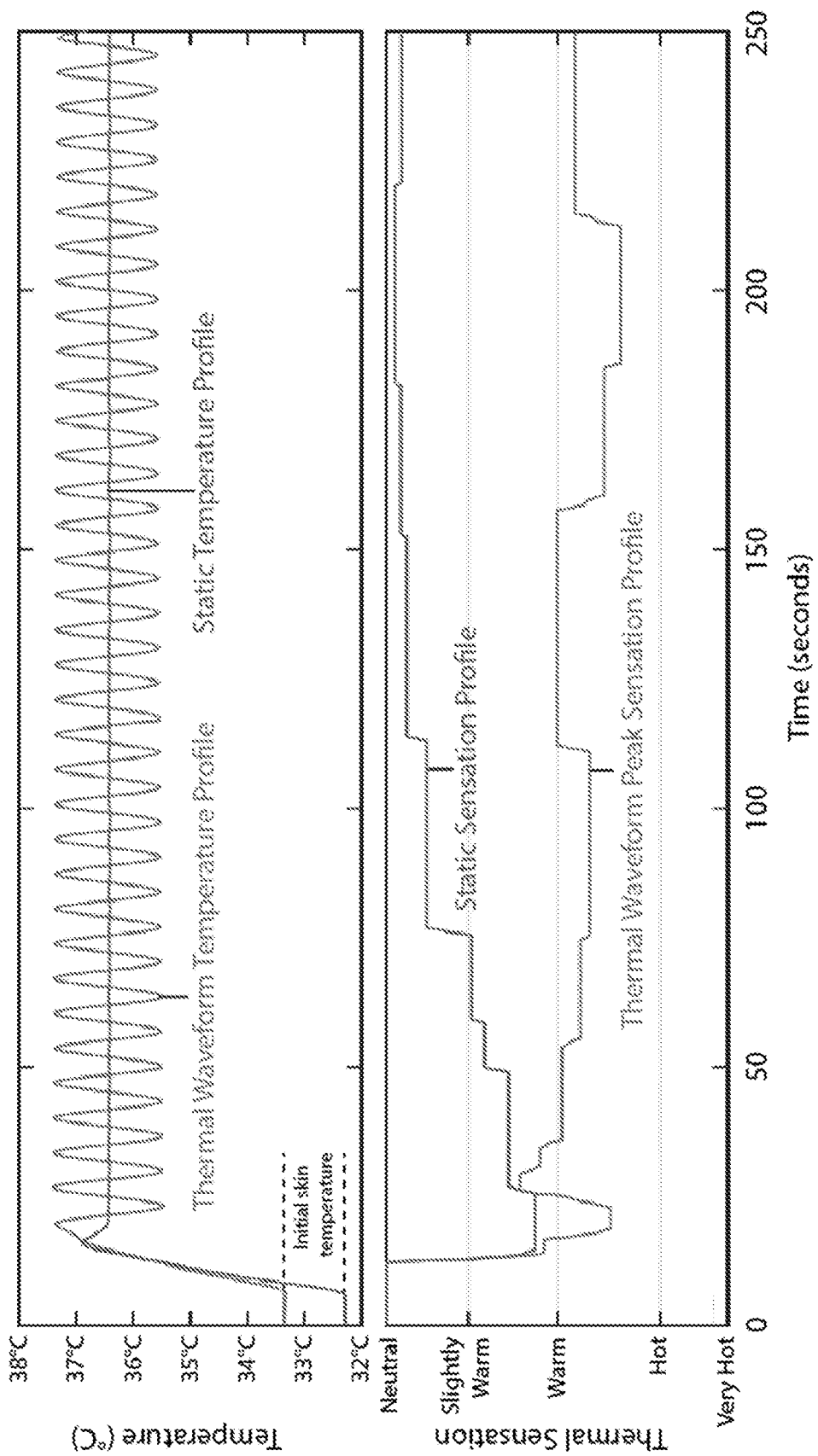
FIG. 6 shows (top) exemplary thermal profiles of a warming thermal profile and a static thermal profile with the same $\Delta T_{AVG}=3°$ C. relative to initial skin temperature and (bottom) thermal sensations generated by alternating profile and static temperature profile over the first 250 seconds are shown.

FIG. 6 compares an alternating warming thermal profile (Thermal Waveform Temperature Profile) to a static temperature profile. In this trial, $\Delta T_{AVG}=3°$ C. for the alternating warming profile and $\Delta T_{AVG}=4°$ C. for the static temperature profile. This discrepancy was believed to favor the ability of the static temperature profile to create a stronger or more lasting thermal sensation, but thermal adaptation was still observed to inhibit the static temperature profile from creating a sustained thermal sensation (FIG. 6). The profile in FIG. 6 is delivering cyclic warming pulses with $\Delta T_{OW}=1.9°$ C. and rates of temperature change >0.1° C./sec. The same trends are observed for warming as were reported for cooling, despite the smaller $\Delta T_{AVG}$ of the profile compared to the static temperature profile. The static temperature profile generates a strong sensation during initialization, but the reported thermal sensation becomes barely perceivable within 90 seconds of experiencing a constant temperature fixed at 4° C. above initial skin temperature. The alternating thermal profile, by leveraging dynamic temperature profiles, created periodic sensations of warmth with relatively consistent sensation levels over the entire 250 second window shown.

In some cases, the exact temperature profiles required may depend strongly on the location(s) and total area of skin being heated or cooled. The general architecture of thermal oscillations, however, can be described and bound by several interrelated parameters. For example, the range of temperatures in which thermal profiles can be applied for therapeutic applications is bound by the hot and cold pain thresholds of the human skin. The pain thresholds vary depending on location, area, and the person's individual thresholds, but the cold pain threshold is approximately 15° C. and the warm pain threshold is approximately 45° C. Skin temperature can vary from 20 to 40° C. but is generally between 33-35° C. Considering these ranges and sources of variability, $\Delta T_{AVG}$ may range between 0° C. and 20° C. from skin temperature for both heating (above skin temperature) and cooling (below skin temperature) to stay within the pain threshold boundaries. The oscillation window, $\Delta T_{OW}$, describes the amplitude of the oscillation and may be controlled within the same temperature range. The amplitude of the thermal oscillations $\Delta T_{OW}$ may therefore range from 0.1° C. (lower bound) to 20° C. (upper bound). The average rate of temperature change during thermal oscillations advantageously should be >0.1° C./sec to avoid adaptation and can, in certain embodiments, be scaled up to 10° C./sec. The oscillations may be assymetric in shape. The thermal oscillations may also exhibit different curvatures and have different average rates of temperature change during ramp up and ramp down, but preferably the oscillations follow the other quantitative boundaries described here. The physiological constraints on the temperature offset ($\Delta T_{AVG}$) and oscillation amplitude ($\Delta T_{OW}$) described thus far may be translated to a range of frequencies that are appropriate for therapeutic thermal profiles in certain embodiments. The period of oscillations used in thermal profiles may vary between 0.02 sec and 400 seconds, which translates to a frequency range of 0.0025 Hz to 50 Hz.

Alternating thermal profiles may be used as a valuable tool for creating consistent warm or cool thermal sensations on human skin over prolonged periods of time. Thermoreceptors in the skin, while prone to adaptation at static temperature profiles, were shown to exhibit predictable and consistent sensations over long periods of time in response to temperature oscillations in which the offset from skin temperature ($\Delta T_{AVG}$) and the oscillation window ($\Delta T_{OW}$) were controlled. This framework for providing consistent thermal stimulation can address the challenges presented by the dynamic response of thermoreceptors to thermal stimuli.

Leveraging alternating thermal profiles to overcome or mitigate adaptation can also result in pronounced physiological effects over many (e.g., 10+) minutes.

Due to the dynamic nature by which thermoreceptors in the skin translate thermal stimuli into thermal sensations, both the rate of temperature change and the difference between the temperature profile and initial skin temperature may contribute to the intensity of the thermal sensation generated. The tuning of alternating thermal profiles to, optionally independently, control intensity of the sensation and the rhythm of the waves, which may be used for maximizing hedonic value of the thermal stimulation given the levels of complexity that drive moment-to-moment variability in an individual's thermal needs, was demonstrated. For example, to finely tune the intensity of thermal sensations, $\Delta T_{AVG}$ may be adjusted with greater than 0.5° C. resolution while keeping $\Delta T_{OW}$ fixed. To adjust the frequency of the oscillations while keeping the sensation constant, the oscillation profile may be adjusted while maintaining the rates of temperature change are >0.1° C./sec and $\Delta T_{AVG}$ and $\Delta T_{OW}$ are held constant.

Figure 7:
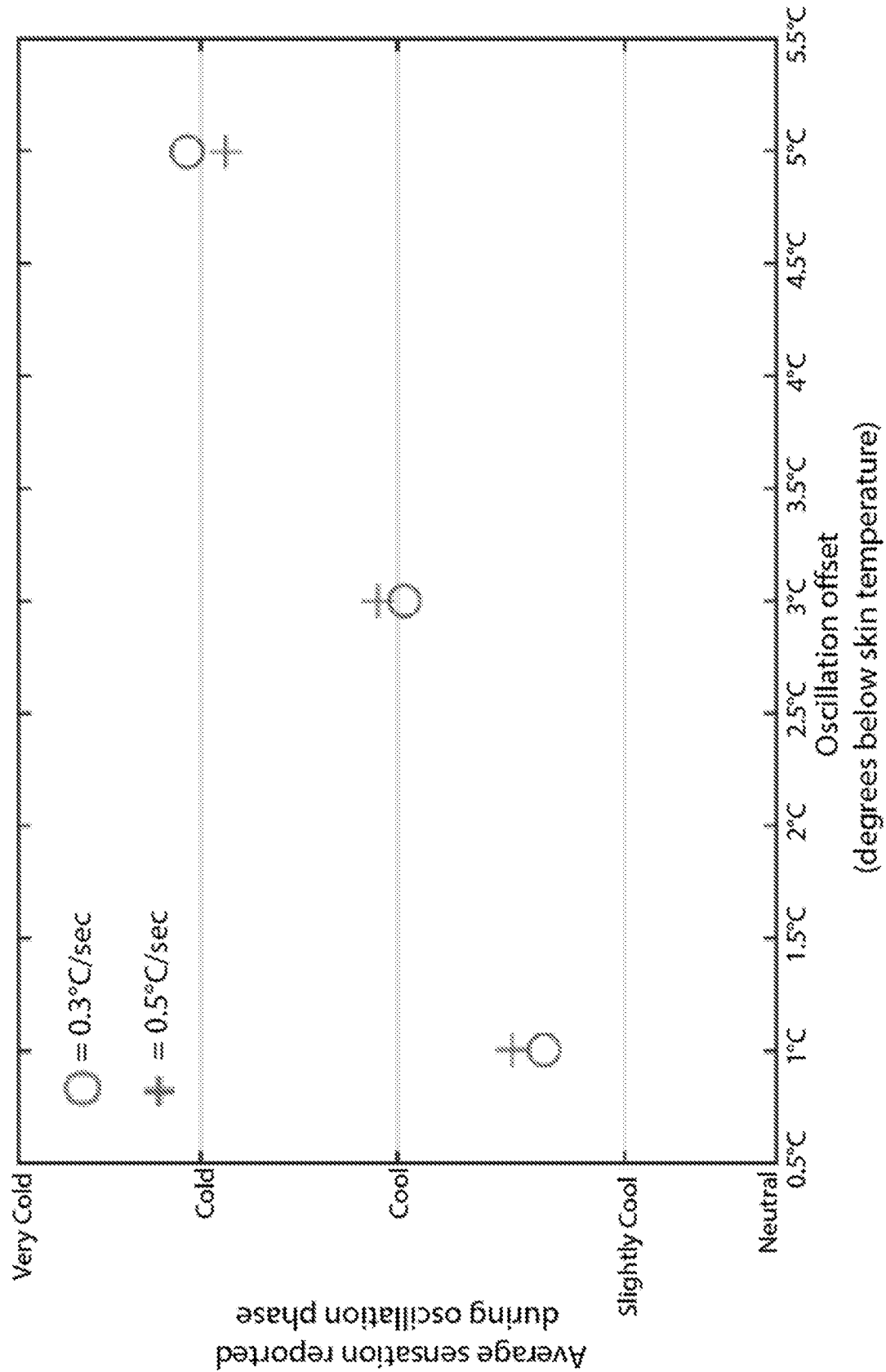
FIG. 7 shows average sensation levels generated by cooling profiles for two different frequencies (peak rates of 0.3° C./sec and 0.5° C./sec) and 3 different temperature offset (the difference between the average temperature and the initial temperature of the surface) levels (1° C., 3° C., 5° C.) according to one set of embodiments.

To illustrate this concept, FIG. 7 shows average sensation levels generated by alternating cooling profiles for two different frequencies (peak rates of 0.3° C./sec and 0.5° C./sec) and 3 different temperature offset (the difference between the average temperature and the initial temperature of the surface) levels (1° C., 3° C., 5° C.). The oscillation window was kept constant throughout these transformations. FIG. 7 shows that the frequency of the oscillation can be tuned without impacting sensation levels by changing the ramp rates but holding the oscillation window constant. If the oscillation window is held constant then the rates of temperature change can be varied from 0.1° C./sec to above 0.5° C./sec without significantly impacting the peak thermal sensation achieved. With respect to tuning the intensity of the thermal sensation, the sensation generally increases linearly with $\Delta T_{AVG}$. When $\Delta T_{OW}$ constant, the sensation generated by a profile can be finely tuned by adjusting $\Delta T_{AVG}$.

The ability for personalized thermal sensations to influence the balance of the autonomic nervous system (ANS) is a fundamental and high-impact lens through which the efficacy of thermal profiles can be quantified, with implications in a wide range of therapeutic and lifestyle applications. Physiological data that shows that localized thermal profiles can trigger physiological responses in the body, in this case the engagement of the ANS, was collected. It should be noted that thermal sensations may also affect a number of other physiological responses, including sudomotor and vasomotor responses. Thermal sensations at the skin can affect skin temperature and blood flow, metabolic rate, respiration and heart rates, and shivering.

To quantify the effect of personalized thermal profiles on the ANS, Heart Rate Variability (HRV) was monitored. HRV was determined by measuring the beat-to-beat heart rate and analyzing variability over time through a frequency domain analysis. In the frequency analysis, the power spectrum of the high-frequency band (HF) (0.15-0.40 Hz) is affected by the parasympathetic nervous system and the low-frequency band (LF) (0.04-0.15 Hz) mainly relates to the activity of the sympathetic nervous system. The ratio of LF and HF can be used to evaluate the relative engagement of the two branches of the ANS. This metric, LF/HF, has been widely used to study the effects of thermal sensations on the balance of the ANS. In these studies, the effect of thermal profiles on the sympathetic and parasympathetic engagement of the ANS was measured using a Polar H7 heart rate sensor and the HRV Expert data analysis package by CardioMood.

Participants were introduced into either a cool room (20° C.) or a warm room (30° C.) and asked to work at a computer in the environmentally controlled room for 25 minutes. The first 15 minutes were used to establish a baseline and then a heating and cooling wristband programmed with a thermal profile was either provided to them for the last 10 minutes (variable) or they continued working in the room without a wristband (control). In the cool condition (20° C. room), the wristband was engaged in a warming mode and in the warm condition (30° C. room) the wristband was provided in cooling mode. The level of heating or cooling received by the participants was not personalized. Rather, a fixed level of warming or cooling was used and the condition of successful "personalization" was determined by subjects ranking the hedonic component of the thermal sensation from the thermal profile as "Moderately Liked" (+2) or greater on a 9 point Likert scale (−4 to +4).

In these trials, Heart Rate Variability of subjects was measured during minutes 10-15 (without heating or cooling) and during minutes 20-25 (with or without a heating and cooling wristband). The effect of the thermal profiles was evaluated as the relative change in LF/HF between the first checkpoint and the second checkpoint and this was compared with the experimental control in which subjects did not have access to localized thermal profiles. A negative ΔLF/HF reflects a shift of the ANS towards parasympathetic engagement (relaxation response) and positive ΔLF/HF indicates a shift towards sympathetic engagement (stress response).

Figure 8A:
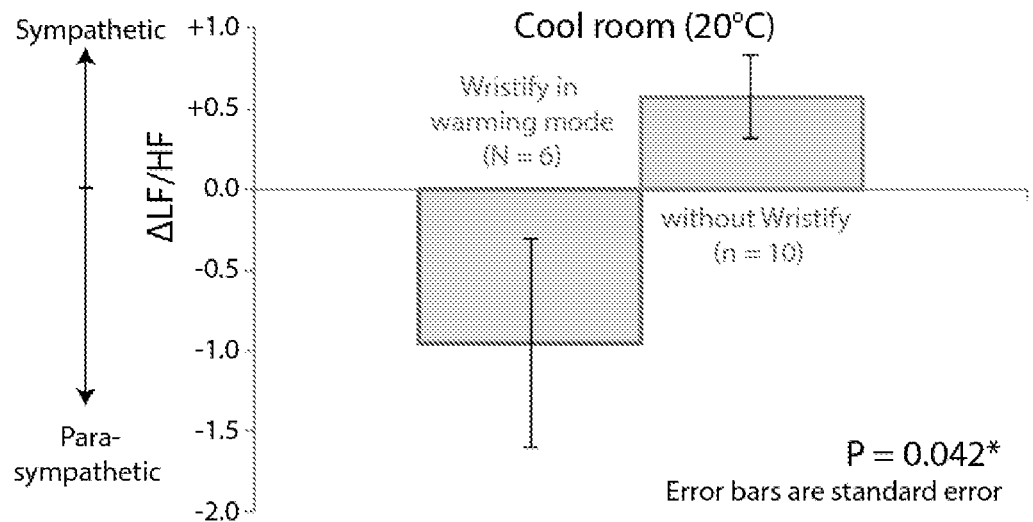
FIG. 8A shows the use of a personalized warming profile in a cool (20 C) room resulted in an average $\Delta LF/HF$ of $-1.0$ normalized units (towards more parasympathetic engagement), compared with an average $\Delta LF/HF$ of $+0.6$ normalized units (towards more sympathetic engagement) without thermal profiles.

The effect of personalized thermal profiles on the autonomic nervous system is shown in FIGS. 8A-9B. As shown in FIGS. 8A and 8B, a statistically significant decrease in LF/HF when subjects were given a personalized profile (heating or cooling) for the last 10 minutes was observed, reflecting a shift towards more parasympathetic engagement (relaxation response) due to the sensations generated by thermal profiles.

Figure 8B:
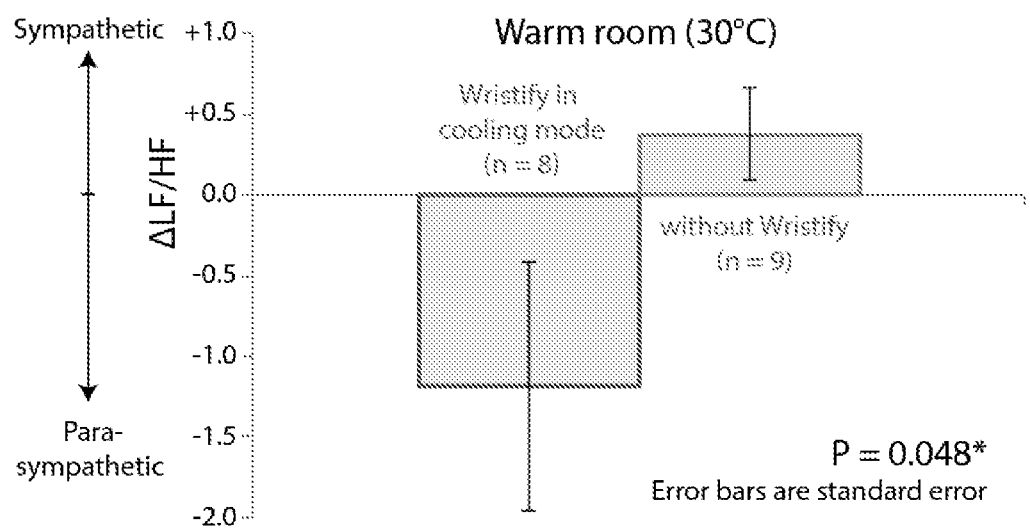
FIG. 8B shows the use of a personalized cooling profile in a warm (30 C) room resulted in an average $\Delta LF/HF$ of $-1.2$ normalized units (towards more parasympathetic engagement), compared with an average $\Delta LF/HF$ of $+0.4$ normalized units (towards more sympathetic engagement) without thermal profiles, according to one set of embodiments.
Figure 9A:
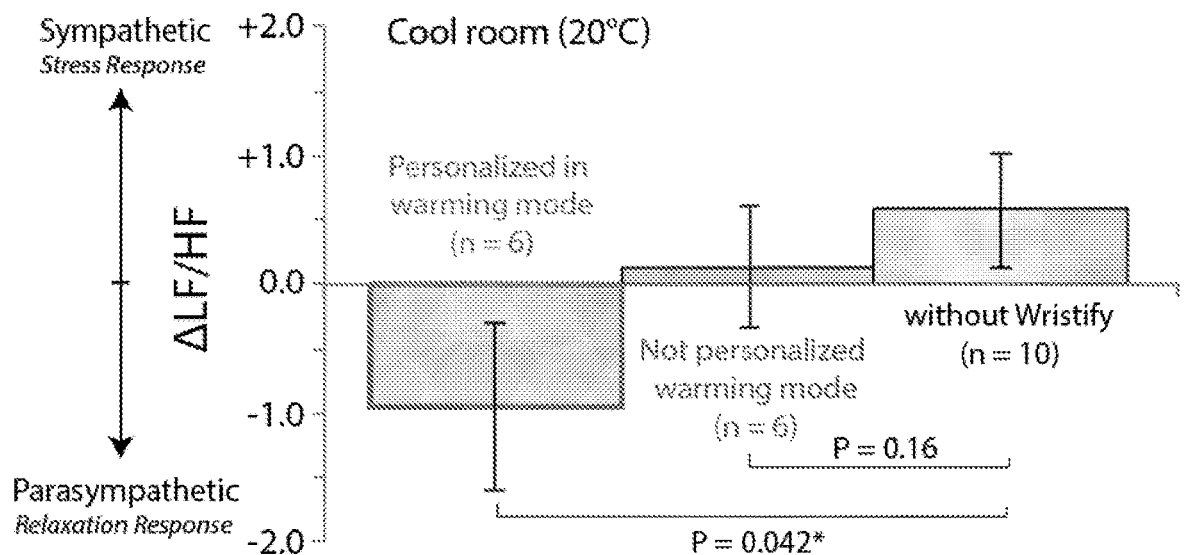
FIG. 9A shows the use of a personalized warming profile in a cool (20 C) room resulted in an average $\Delta LF/HF$ of $-1.0$ normalized units (towards more parasympathetic engagement), compared with an average $\Delta LF/HF$ of $+0.6$ normalized units (towards more sympathetic engagement) without thermal profiles.
Figure 9B:
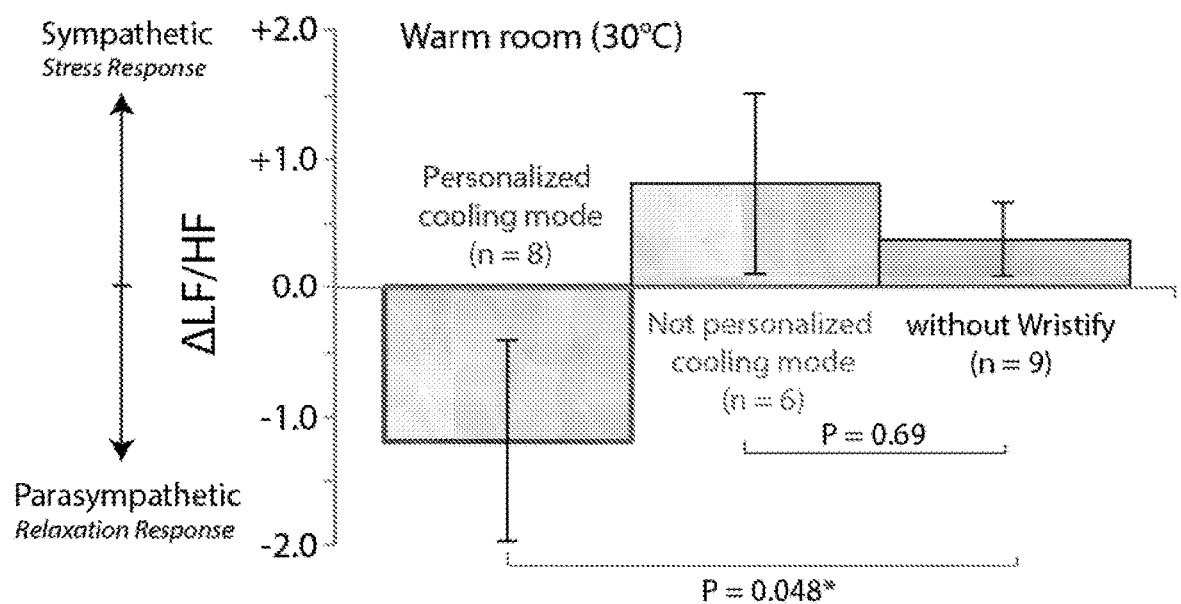
FIG. 9B shows the use of a personalized cooling profile in a warm (30 C) room resulted in an average $\Delta LF/HF$ of $-1.2$ normalized units (towards more parasympathetic engagement), compared with an average $\Delta LF/HF$ of $+0.4$ normalized units (towards more sympathetic engagement) without thermal profiles.

FIGS. 9A-9B shows the data collected from similar experiments as those conducted and shown in FIGS. 8A-8B, but including LF/HF for subjects who were provided with a heating and cooling wristband but did not report the thermal sensation as +2 or greater on a 9 point likert scale (−4 to +4). While the subjects felt the thermal sensations from the wrist band, the intensity of the heating or cooling sensation was not sufficiently personalized for strong hedonic value. FIGS. 9A-9B show that subjects for whom the level of heating or cooling was not within their "sweet spot" did not exhibit a statistically significant change compared with control under either condition.

The alternating thermal profiles provided according to certain embodiments of the invention can provides researchers and users precise control over thermal sensations applied directly to the skin. In some cases, this approach may allow people to influence their autonomic nervous system by harnessing the power of personalized thermal sensations. Such physiological data (e.g., FIGS. 8A-9B) and existing psychophysiological research into thermal sensations suggest that the implications of alternating thermal profiles as a therapy tool are extremely broad. For example, such thermal profiles may have the ability to help people manage the symptoms or side effects of conditions including, but not limited to, Thermal discomfort, Hot flashes, Insomnia, Chronic pain, Dysautonomia, Anxiety, Panic Attacks, Depression, and PTSD.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Any terms as used herein related to shape, orientation, alignment, and/or geometric relationship of or between, for example, one or more articles, structures, forces, fields, flows, directions/trajectories, and/or subcomponents thereof and/or combinations thereof and/or any other tangible or intangible elements not listed above amenable to characterization by such terms, unless otherwise defined or indicated, shall be understood to not require absolute conformance to a mathematical definition of such term, but, rather, shall be understood to indicate conformance to the mathematical definition of such term to the extent possible for the subject matter so characterized as would be understood by one skilled in the art most closely related to such subject matter. Examples of such terms related to shape, orientation, and/or geometric relationship include, but are not limited to terms descriptive of: shape—such as, round, square, circular/circle, rectangular/rectangle, triangular/triangle, cylindrical/cylinder, elliptical/ellipse, (n)polygonal/(n)polygon, etc.; angular orientation—such as perpendicular, orthogonal, parallel, vertical, horizontal, collinear, etc.; contour and/or trajectory—such as, plane/planar, coplanar, hemispherical, semi-hemispherical, line/linear, hyperbolic, parabolic, flat, curved, straight, arcuate, sinusoidal, tangent/tangential, etc.; direction—such as, north, south, east, west, etc.; surface and/or bulk material properties and/or spatial/temporal resolution and/or distribution—such as, smooth, reflective, transparent, clear, opaque, rigid, impermeable, uniform(ly), inert, non-wettable, insoluble, steady, invariant, constant, homogeneous, etc.; as well as many others that would be apparent to those skilled in the relevant arts. As one example, a fabricated article that would described herein as being "square" would not require such article to have faces or sides that are perfectly planar or linear and that intersect at angles of exactly 90 degrees (indeed, such an article can only exist as a mathematical abstraction), but rather, the shape of such article should be interpreted as approximating a "square," as defined mathematically, to an extent typically achievable and achieved for the recited fabrication technique as would be understood by those skilled in the art or as specifically described. As another example, two or more fabricated articles that would described herein as being "aligned" would not require such articles to have faces or sides that are perfectly aligned (indeed, such an article can only exist as a mathematical abstraction), but rather, the arrangement of such articles should be interpreted as approximating "aligned," as defined mathematically, to an extent typically achievable and achieved for the recited fabrication technique as would be understood by those skilled in the art or as specifically described.

What is claimed:

1. A device for manipulating a temperature of a surface, comprising:
    at least one heating and/or cooling element constructed and arranged to be disposed adjacent the surface; and
    a processor in electrical communication with the at least one heating and/or cooling element, the processor configured to cause the at least one heating and/or cooling element to generate a thermal profile at a region of the at least one heating and/or cooling element adjacent the surface, the thermal profile comprising a first portion comprising a ramp profile, a second portion comprising a first alternating temperature profile, and at least a third portion comprising at least a second alternating temperature profile, different than the first alternating temperature profile, wherein the ramp profile comprises an initial temperature and a setpoint temperature, wherein the processor is configured to initiate the ramp profile in response to a first user input and set the setpoint temperature in response to a second user input during the ramp profile, wherein the first user input is a press of a button and the second user input is a release of the button.

2. The device of claim 1, wherein the processor is configured to set the setpoint temperature to a temperature of the ramp profile at a predetermined time before the second user input.

3. The device of claim 1, wherein the first alternating temperature profile comprises a first average temperature, a first average frequency, and a first oscillation window.

4. The device of claim 3, wherein the second alternating temperature profile comprises a second average temperature different than the first average temperature, a second average frequency different than the first average frequency, and/or a second oscillating window different than the first oscillation window.

5. The device of claim 1, wherein a temperature of the thermal profile throughout a duration of the second portion and the third portion of the temperature profile is greater than the initial temperature.

6. The device of claim 1, wherein a temperature of the thermal profile throughout a duration of the second portion and the third portion of the temperature profile is less than the initial temperature.

7. The device of claim 1, wherein the first alternating temperature profile and the second alternating temperature profile vary with respect to time.

8. A device for manipulating a temperature of a surface, comprising:
    at least one heating and/or cooling element constructed and arranged to be disposed adjacent the surface; and
    a processor in electrical communication with the at least one heating and/or cooling element, the processor configured to cause the at least one heating and/or cooling element to generate an alternating thermal profile at a region of the at least one heating and/or cooling element adjacent the surface, the alternating thermal profile comprising an average temperature, an average frequency, and an oscillation window, wherein the processor is configured to modify at least one of the average temperature, the average frequency, and the oscillation window, wherein the processor is configured to receive a signal from a user, wherein the signal is configured to cause the processor to modify at least one of the average temperature, the average frequency, and the oscillation window, wherein the signal includes a first user input and a second user input, wherein the processor is configured to initiate a ramp profile portion of the alternating thermal profile in response to the first user input and set the average temperature in response to the second user input during the ramp profile portion of the alternating thermal profile.

9. The device of claim 8, wherein the processor is configured to receive a signal from a sensor, wherein the signal is configured to cause the processor to modify at least one of the average temperature, the average frequency, and the oscillation window.

10. The device of claim 9, wherein the sensor is at least one selected from the group of a temperature sensor, physiological sensor, biometric sensor, accelerometer, and environmental sensor.

11. The device of claim 8, wherein the processor is configured to set the average temperature to a temperature of the alternating thermal profile at a predetermined time before the second user input.

12. The device of claim 8, wherein the first user input is a press of a button and the second user input is a release of the button.

13. The device of claim 8, wherein the alternating thermal profile varies with respect to time.

14. A method for manipulating a temperature of a surface, comprising:

positioning a region of at least one heating and/or cooling element adjacent to the surface; and generating a thermal profile at the region of the at least one heating and/or cooling element adjacent the surface, wherein generating the thermal profile includes:

generating a first thermal profile portion comprising a ramp profile;

generating a second thermal profile portion comprising a first alternating temperature profile;

generating a third thermal profile portion comprising a second alternating temperature profile different than the first alternating temperature profile, wherein the ramp profile comprises an initial temperature and a setpoint temperature; and initiating the ramp profile in response to a first user input and setting the setpoint temperature in response to a second user input during the ramp profile.

15. The method of claim 14, further comprising setting the setpoint temperature to a temperature of the ramp profile at a predetermined time before the second user input.

16. The method of claim 14, wherein the first alternating temperature profile comprises a first average temperature, a first average frequency, and a first oscillation window.

17. The method of claim 16, wherein the second alternating temperature profile comprises a second average temperature different than the first average temperature, a second average frequency different than the first average frequency, and/or a second oscillating window different than the first oscillation window.

18. The method of claim 14, wherein the first user input is a press of a button and the second user input is a release of the button.

19. The method of claim 14, wherein a temperature of the thermal profile throughout a duration of the second thermal profile portion and the third thermal profile portion is greater than the initial temperature.

20. The method of claim 14, wherein a temperature of the thermal profile throughout a duration of the second thermal profile portion and the third thermal profile portion is less than the initial temperature.

21. The method of claim 14, wherein the first alternating temperature profile and the second alternating temperature profile vary with respect to time.

* * * * *